(12) United States Patent
Nseir Manassa et al.

(10) Patent No.: US 10,478,519 B2
(45) Date of Patent: Nov. 19, 2019

(54) TISSUE SUBSTITUTE MULTILAYER MATRIX AND USES THEREOF

(71) Applicant: Nurami Medical Ltd, Nazareth (IL)

(72) Inventors: Nora Nseir Manassa, Haifa (IL); Amir Bahar, Kiryat-Tivon (IL)

(73) Assignee: NURAMI MEDICAL LTD., Nazareth (IL)

( * ) Notice: Subject to any disclaimer, the term of this patent is extended or adjusted under 35 U.S.C. 154(b) by 575 days.

(21) Appl. No.: 15/102,966

(22) PCT Filed: Dec. 17, 2014

(86) PCT No.: PCT/IL2014/051109
§ 371 (c)(1),
(2) Date: Jun. 9, 2016

(87) PCT Pub. No.: WO2015/092797
PCT Pub. Date: Jun. 25, 2015

(65) Prior Publication Data
US 2017/0072089 A1 Mar. 16, 2017

Related U.S. Application Data

(60) Provisional application No. 61/916,829, filed on Dec. 17, 2013.

(51) Int. Cl.
*A61L 15/26* (2006.01)
*B29C 48/00* (2019.01)
(Continued)

(52) U.S. Cl.
CPC ............. *A61L 15/26* (2013.01); *A61L 15/425* (2013.01); *A61L 17/12* (2013.01);
(Continued)

(58) Field of Classification Search
CPC ....... C08L 67/04; C08L 71/02; D01D 5/0076; D01D 5/0007; A61L 2430/00;
(Continued)

(56) References Cited

U.S. PATENT DOCUMENTS

| 5,861,034 A | 1/1999 | Taira et al. |
| 6,514,291 B1 | 2/2003 | Yamauchi et al. |

(Continued)

FOREIGN PATENT DOCUMENTS

| CN | 101507661 A | 8/2009 |
| EP | 1741456 | 1/2007 |

(Continued)

OTHER PUBLICATIONS

Keisuke Yamada et al., "Development of a dural substitute from synthetic bioabsorbable polymers", Journal of Neurosurgery, American Association of Neurological Surgeons, US, vol. 86, No. 6, p. 1012-1017, 1997.

(Continued)

*Primary Examiner* — Camie S Thompson
(74) *Attorney, Agent, or Firm* — The Roy Gross Law Firm, LLC; Roy Gross

(57) ABSTRACT

Compositions-of-matter comprising a matrix made of one or more, preferably two or more elastic layers and one or more viscoelastic layer are disclosed. The compositions-of-matter are characterized by high water-impermeability and optionally by self-recovery. Processes of preparing the compositions-of-matter and uses thereof as tissue substitutes or for repairing damaged tissues are also disclosed.

33 Claims, 4 Drawing Sheets

(51) Int. Cl.
| | |
|---|---|
| *B29C 48/14* | (2019.01) |
| *B32B 5/26* | (2006.01) |
| *A61L 15/42* | (2006.01) |
| *B32B 5/02* | (2006.01) |
| *A61L 17/12* | (2006.01) |
| *B29C 65/00* | (2006.01) |
| *B32B 5/12* | (2006.01) |
| *B32B 7/02* | (2019.01) |
| *B32B 37/10* | (2006.01) |
| *B32B 37/14* | (2006.01) |
| *A61F 2/00* | (2006.01) |
| *B29K 67/00* | (2006.01) |
| *B29K 667/00* | (2006.01) |
| *B29L 31/00* | (2006.01) |

(52) U.S. Cl.
CPC ........ *B29C 48/0021* (2019.02); *B29C 48/022* (2019.02); *B29C 48/142* (2019.02); *B29C 66/45* (2013.01); *B29C 66/7315* (2013.01); *B32B 5/022* (2013.01); *B32B 5/12* (2013.01); *B32B 5/26* (2013.01); *B32B 7/02* (2013.01); *B32B 37/10* (2013.01); *B32B 37/144* (2013.01); *A61F 2/0063* (2013.01); *B29K 2067/04* (2013.01); *B29K 2067/046* (2013.01); *B29K 2667/04* (2013.01); *B29K 2667/046* (2013.01); *B29K 2995/0046* (2013.01); *B29L 2031/7532* (2013.01); *B32B 2250/03* (2013.01); *B32B 2250/20* (2013.01); *B32B 2250/244* (2013.01); *B32B 2250/40* (2013.01); *B32B 2262/0276* (2013.01); *B32B 2307/51* (2013.01); *B32B 2367/00* (2013.01); *B32B 2535/00* (2013.01)

(58) Field of Classification Search
CPC ...... A61L 15/425; A61L 27/56; A61L 31/146; D05D 5/0007; A61F 2/0063; B29C 48/0021; B29K 2067/04; B29K 2067/06; B29K 667/04; B29K 667/046; B29K 2995/0046; B29L 2031/7532; B32B 2250/03; B32B 2250/20; B32B 2250/244; B32B 2250/40; B32B 2255/101; B32B 2262/0253; B32B 2262/0261; B32B 2262/0276; B32B 2037/51; B32B 2535/00; B32B 37/144; B32B 5/26

USPC ............ 425/174.8 E; 623/23.72, 23.75, 920; 264/241; 523/113; 606/151; 428/292.1; 424/422, 423
See application file for complete search history.

(56) References Cited

U.S. PATENT DOCUMENTS

| | | |
|---|---|---|
| 7,736,393 B2 | 6/2010 | Shirahama et al. |
| 8,795,708 B2 | 8/2014 | Xu et al. |
| 2009/0004239 A1 | 1/2009 | Ladet et al. |
| 2010/0233115 A1 | 9/2010 | Patel et al. |
| 2012/0029654 A1 | 2/2012 | Xu et al. |
| 2013/0197663 A1 | 8/2013 | MacEwan et al. |

FOREIGN PATENT DOCUMENTS

| | | |
|---|---|---|
| EP | 2163269 | 3/2010 |
| EP | 2218466 A1 | 8/2010 |
| WO | WO 2015/092797 | 6/2015 |

OTHER PUBLICATIONS

International Preliminary Report on Patentability dated Jun. 30, 2016 From the International Bureau of WIPO Re. Application No. PCT/IL2014/051109.

International Search Report and the Written Opinion dated Mar. 24, 2015 From the International Searching Authority Re. Application No. PCT/IL2014/051109.

Kurpinski et al. "Dura Mater Regeneration With A Novel Synthetic, Bilayered Nanofibrous Dural Substitute: An Experimental Study", Nanomedicine, 6(2): 325-337, Feb. 2011.

Mukai et al. "Development of Watertight and Bioabsorbable Synthetic Dural Substitutes", Artificial Organs, 32(6): 473-483, Published Online Apr. 16, 2008. Abstract, Figs.1, 3, p. 474, "Materials and Metods", Tables.

Wang et al. "Multilayer Scaffold of Electrospun PLA-PCL-Collagen Nanofibers as A Dural Substitute", Journal of Biomedical Material Research, Part B: Applied Biomaterials, 101(8): 1359-1366, Epub May 17, 2013.

Xie et al. "Radially Aligned, Electrospun Nanofilbers as Dural Substitutes for Wound Closure and Tissue Regeneration Applications", ACS Nano, 4(9): 5027-5036, Published Online Aug. 9, 2010. Abstract, p. 5028.

TISSUE SUBSTITUTE MULTILAYER MATRIX AND USES THEREOF

RELATED APPLICATIONS

This application is a National Phase of PCT Patent Application No. PCT/IL2014/051109 having International filing date of Dec. 17, 2014, which claims the benefit of priority under 35 USC § 119(e) of U.S. Provisional Patent Application No. 61/916,829 filed on Dec. 17, 2013. The contents of the above applications are all incorporated by reference as if fully set forth herein in their entirety.

FIELD AND BACKGROUND OF THE INVENTION

The present invention, in some embodiments thereof, relates to tissue substitutes, and more particularly, but not exclusively, to an elastic layered matrix and to uses thereof as a tissue substitute.

Leakage of liquid or air from or into damaged tissue is a potentially life-threatening condition which may occur as a result of a wide variety of circumstances, including surgery and traumatic injury.

The dura mater, also referred to herein and in the art simply as "dura", is a thin membrane that surrounds the brain and spinal cord, and which is responsible for containment of the cerebrospinal fluid. The dura mater may be damaged as a result of traumatic injury or of a surgical operation requiring access to underlying nervous tissue (e.g., open cranial neurosurgery, spinal surgery). When the dura mater is damaged, a dural substitute in a form of a patch may be needed to prevent leakage of cerebrospinal fluid, prevent infection, and promote tissue regrowth (e.g., dura mater regeneration). Background Art FIG. 8 schematically depicts such a use of a dural substitute.

Materials which have been used as dural substitutes include autologous tissue grafts (such as temporal fascia, fascia lata femoris and periosteal flaps), allografts (such as lyophilized cadaveric dural grafts), xenografts (such as bovine pericardium and porcine small intestinal submucosa), and natural and synthetic polymers, such as poly (lactic acid), poly(ε-caprolactone), expanded poly(tetrafluoroethylene), polyurethane, poly(ethylene glycol), poly (hydroxyethyl methacrylate), collagen, gelatin, fibrinogen and alginate [Wang et al., *J Biomed Mater Res B Applied Biomater* 2013, 101:1359-1366].

Collagen-based matrices, such as Duragen® matrices and other branded products, have become widely used, as they promote cell ingrowth and tissue integration, and under certain conditions can be implanted without sutures by simply being onlaid. The collagen in such matrices is typically animal-derived. However, such matrices exhibit low tensile strength, frequently leak, and are unsuitable for being sutured if necessary [Kurpinski & Patel, *Nanomedicine* 2011, 6:325-337; Wang et al., *J Biomed Mater Res B Applied Biomater* 2013, 101:1359-1366]. Use of collagen-based dural substitutes is associated with post-surgical infections in 15-20% of patients. The use of additional products, such as liquid sealants, for overcoming the shortcomings of collagen-based matrices can complicate an operation and increase costs.

Kurpinski & Patel [*Nanomedicine* 2011, 6:325-337] describe a bilayered synthetic nanofibrous dura mater substitute fabricated from blended electrospun fibers of poly (DL-lactide-co-ε-caprolactone) (in a 70:30 ratio) and poly (propylene glycol). The bilayered design comprises an aligned nanofiber layer which is reported to promote cell guidance and healing, and a random nanofiber layer for enhancing mechanical integrity. The bilayered structure was formed by electrospinning in a manner such that a single continuous fiber is initially deposited in a predominantly aligned orientation, and later deposited in a predominantly random orientation.

Wang et al. [*J Biomed Mater Res B Applied Biomater* 2013, 101:1359-1366] describe a dural substitute fabricated by electrospinning, comprising an inner layer composed of poly(lactic acid) for reducing tissue adhesion, a middle layer composed of poly(ε-caprolactone) and poly(lactic acid) for providing water-tightness, and an outer layer comprising collagen for promoting cell attachment.

U.S. Pat. No. 8,795,708 describes an artificial dura mater comprising electrospun layers, including at least one hydrophobic electrospun layer, and optionally at least one hydrophilic layer. The hydrophobic layer is intended to be placed proximate to the brain surface to take advantage of its anti-adhesion capability, whereas the hydrophilic layer is intended to be placed distant to the brain for serving as a scaffold for cells.

U.S. Patent Application Publication No. 2009/0004239 describes multilayer structures for dural repair, including a porous layer, such as a collagen containing foam; and a non-porous layer, such as a collagen film, having a reinforcement member, such as a mesh.

U.S. Pat. No. 6,514,291 describes an artificial dura mater comprising at least one sheet of a synthetic polymer, such as a lactide/ε-caprolactone copolymer, having a storage elastic modulus of $10^7$ to $5 \times 10^8$ Pa at 37° C. The sheet can be produced by dissolving a lactide/ε-caprolactone copolymer (in a molar ratio ranging from 40:60 to 60:40) in a solvent, filtering and casting the resultant solution, followed by air drying. Three layer structures comprising a reinforcement synthetic polymer sandwiched between two of the aforementioned sheets are also described therein.

European Patent No. 1741456 describes an artificial dura mater comprising a laminate of at least two layers, at least one of which is formed of a lactic acid/glycolic acid/ε-caprolactone copolymer having a molar ratio of 60-85% lactic acid, 3-15% glycolic acid, and 10-30% ε-caprolactone.

European Patent No. 2163269 describes an artificial dura mater comprising an amorphous or low-crystallinity polymer, such as a copolymer of L-lactic acid and ε-caprolactone, and a structural reinforcement. The amorphous or low crystallinity polymer is characterized by a low elastic modulus ($10^8$ Pa or less at 37° C.) and high relaxation elastic modulus (30% or more of the elastic modulus), in order to prevent leakage after suturing.

U.S. Patent Application Publication No. 2010/0233115 describes a fibrous polymer scaffold having a first layer of aligned polymer fibers, a second layer of polymer fibers, and optionally additional layers. The second layer can include unaligned or randomly oriented fibers, or fibers that are aligned and offset from the average axis of alignment of the first layer.

Additional background art includes U.S. Patent Application Publication No. 2013/0197663.

SUMMARY OF THE INVENTION

Based on information gathered from several resources, including practicing surgeons, the present inventors have envisioned that it would be advantageous for a matrix used as a dural substitute to exhibit the following features: a)

ability to create a tight seal to prevent cerebrospinal fluid leakage; b) mechanical strength sufficient for enabling robust suturing or stapling; c) capability of recovering upon formation of a suture or a staple hole; d) flexibility for conforming to complex surfaces without creasing; e) ability to be cut with a simple scissors and in general, easy to handle; f) ability to integrate into existing dura mater without adhering to neural tissue; g) biodegradability characterized by a controlled rate of degradation (which balances tissue growth and "creeping" of growing tissue into the matrix); h) ability to enhance damaged tissue regrowth, in order to support wound healing and recuperation; i) biocompatibility for reducing or preventing rejection and/or development of local inflammation; and j) ability to reduce risk of bacterial or viral infection. Such properties would overcome many shortcomings of existing dural substitutes.

According to an aspect of some embodiments of the present invention there is provided a composition-of-matter comprising a multi-layer matrix, the matrix comprising at least one layer of an elastic polymeric material and at least one layer of a viscoelastic polymeric material.

According to some embodiments, the matrix contains two of the layers of an elastic polymeric material, and one of the layers of a viscoelastic polymeric material interposed between the layers of an elastic polymeric material.

According to an aspect of some embodiments of the present invention there is provided a composition-of-matter comprising a multi-layer matrix, the matrix comprising at least two layers of an elastic polymeric material and at least one layer of a viscoelastic polymeric material interposed between two of the layers of an elastic polymeric material.

According to an aspect of some embodiments of the present invention there is provided a multi-layer matrix comprising at least one layer of an elastic polymeric material and at least one layer of a viscoelastic polymeric material, the matrix being characterized by a water-permeability of less than 1 ml per hour per cm$^2$ upon exposure to an aqueous liquid at a pressure of 40 mmHg.

According to some of any of the embodiments and/or aspect of the present invention, a layer of the viscoelastic polymeric material comprises a polymer characterized by a glass transition temperature and/or melting point at a temperature below 40° C.

According to some of any of the embodiments and/or aspect of the present invention, one or more of the layers of the elastic polymeric material is in a form of a porous layer of polymeric fibers, and/or is made of polymeric fibers.

According to some embodiments, each of the layers of an elastic polymeric material is independently made of polymeric fibers.

According to some of any of the embodiments of the present invention, one or more, or each of the layers of the elastic polymeric material is characterized by porosity higher than 50%, as defined herein.

According to some of any of the embodiments of the present invention, one or more, or each of the layers of the elastic polymeric material is characterized by a porosity higher than 50%, as defined herein, and the one or more layers of the viscoelastic polymeric material is characterized by a lower porosity, e.g., lower than 50% or lower than 30%, or lower than 20%, or lower than 10%, or even as non-porous.

According to some of any one of the embodiments and/or aspect of the present invention, at least two layers of the elastic polymeric material, each of the layers is independently in a form of a porous layer of polymeric fibers, wherein the layer of a viscoelastic polymeric material is interposed between two of the layers of an elastic polymeric material.

According to some of any one of the embodiments and/or aspect of the present invention, the elastic polymeric material comprises a polymer characterized by a glass transition temperature and/or melting point at a temperature above 40° C.

According to some embodiments of the present invention there is provided a composition-of-matter comprising a multi-layer matrix, the matrix comprising at least one layer of an elastic polymeric material and at least one layer of a viscoelastic polymeric material, wherein each of said viscoelastic polymeric material and the elastic polymeric material independently comprises a polymer characterized by a glass transition temperature and/or melting point at a temperature above 40° C.

According to some of any of the embodiments and/or aspects of the present invention, the layer of a viscoelastic polymeric material is characterized by a loss tangent (G"/G') at a temperature of 10° C. and frequency of 0.1 Hz which is in a range of from 0.01 to 4.

According to some of any of the embodiments and/or aspects of the present invention, one or more of, or each layer of the elastic polymeric material is a porous layer characterized by a porosity of at least 50%.

According to some of any of the embodiments and/or aspects of the present invention, the polymeric fibers are characterized by a mean diameter in a range of from 0.001 to 30 μm.

According to some of any of the embodiments and/or aspects of the present invention, the layer of a viscoelastic polymeric material is characterized by at least one of:
a) a storage shear modulus (G') in a range of from 0.01 to 10 MPa, at a temperature of 10° C. and frequency of 0.1 Hz; and
b) a loss shear modulus (G") in a range of from 0.0001 to 2 MPa, at a temperature of 10° C. and frequency of 0.1 Hz.

According to some of any of the embodiments and/or aspects of the present invention, the matrix is characterized by a thickness of less than 3 mm.

According to some of any of the embodiments and/or aspects of the present invention, a layer of the polymeric fibers is characterized by a thickness in a range of from 10 to 500 μm.

According to some of any of the embodiments and/or aspects of the present invention, the polymeric fibers comprise electrospun elastic polymeric material.

According to some of any of the embodiments and/or aspects of the present invention, the matrix is characterized by an elastic modulus which is similar (+/−20%) to the elastic modulus of the later of the elastic polymeric material.

According to an aspect of some embodiments of the present invention there is provided a composition-of-matter comprising a multi-layer matrix, the matrix comprising at least one layer of an elastic polymeric material and at least one layer of a viscoelastic polymeric material, wherein a layer of the viscoelastic polymeric material is characterized by a loss tangent (G"/G') at a temperature of 10° C. and frequency of 0.1 Hz which is in a range of from 0.01 to 4.

According to an aspect of some embodiments of the present invention there is provided a composition-of-matter comprising a multi-layer matrix, the matrix comprising at least one layer of an elastic polymeric material and at least one layer of a viscoelastic polymeric material, wherein a layer of the viscoelastic polymeric material is characterized by a loss tangent (G"/G') at a temperature of 10° C. and frequency of 0.1 Hz which is in a range of from 0.01 to 4, and wherein the at least one layer of an elastic polymeric material is a porous layer characterized by a porosity of at least 50%.

According to some of any of the embodiments and/or aspects of the present invention, the at least one layer of an elastic polymeric material comprises polymeric fibers, as described herein.

According to some of any of these embodiments of the present invention, at least one layer of the viscoelastic polymeric material is interposed between two layers of the elastic polymeric material.

According to some of any of these embodiments of the present invention, the matrix contains two of the layers of an elastic polymeric material, and one of the layers of a viscoelastic polymeric material interposed between the layers of an elastic polymeric material.

According to some of any of these embodiments of the present invention, the layer of a viscoelastic polymeric material is characterized by at least one of: a) a storage shear modulus (G') in a range of from 0.01 to 10 MPa, at a temperature of 10° C. and frequency of 0.1 Hz; b) a loss shear modulus (G") in a range of from 0.0001 to 2 MPa, at a temperature of 10° C. and frequency of 0.1 Hz; and c) a glass transition temperature and/or melting point of the viscoelastic polymeric material which is at a temperature below 40° C.

According to some of any of the embodiments and/or aspects of the present invention, the layer of a viscoelastic polymeric material is characterized by a thickness in a range of from 1 to 300 µm.

According to some of any of the embodiments and/or aspects of the present invention, the layer of a viscoelastic polymeric material is characterized by porosity in a range of from 0 to 50%.

According to some of any of the embodiments and/or aspects of the present invention, the elastic polymeric material is biocompatible.

According to some of any of the embodiments and/or aspects of the present invention, each of the elastic polymeric material and the viscoelastic polymeric material is made of a biocompatible and biodegradable polymer. Alternatively one or both polymeric materials are non-degradable.

According to some of any of the embodiments and/or aspects of the present invention, the matrix is characterized by a thickness of less than 3 mm.

According to some of any of the embodiments and/or aspects of the present invention, each of the layers of an elastic polymeric material is characterized by a thickness in a range of from 10 to 500 µm.

According to some of any of the embodiments and/or aspects of the present invention, the elastic polymeric material comprises a polymer characterized by a glass transition temperature and/or melting point at a temperature above 40° C.

According to some of any of the embodiments and/or aspects of the present invention, one or more of, or each of the layers of an elastic polymeric material is characterized by an elastic modulus in a range of from 1 kPa to 1 GPa.

According to some of any of the embodiments and/or aspects of the present invention, one or more of, or each of the layers of an elastic polymeric material is characterized by an elongation at failure of at least 100%.

According to some of any of the embodiments and/or aspects of the present invention, one or more of, or each of the layers of an elastic polymeric material is characterized by an ultimate tensile strength of at least 0.05 MPa.

According to some of any of the embodiments and/or aspects of the present invention, one or more of, or each of the layers of an elastic polymeric material is characterized by a recovery of at least 75%.

According to some of any of the embodiments and/or aspects of the present invention, the matrix is characterized by an elastic modulus which is within a range of 80% to 120% of an elastic modulus of at least one of the elastic layers.

According to some of any of the embodiments and/or aspects of the present invention, the one or more layers of an elastic polymeric material are each independently formed of a polymeric material selected from the group consisting of a polyester, a polyanhydride, a polyacetal, a polyorthoester, a polyurethane, a polycarbonate, a polyphosphazene, a polyphosphoester, a polyether, a silicone, a polyamide, a polysulfone, a polyether ether ketone (PEEK), poly(ethylene glycol), polytetrafluoroethylene, polyethylene, poly(methyl methacrylate), poly(ethyl methacrylate), poly(methyl acrylate), poly(ethyl acrylate), a polypeptide, a polysaccharide and copolymers thereof.

According to some of any of the embodiments and/or aspects of the present invention, the polyester is selected from the group consisting of poly(lactic acid), poly(ε-caprolactone), poly(glycolic acid), poly(trimethylene carbonate), poly(ethylene terephthalate), polydioxanone and copolymers thereof.

According to some of any of the embodiments and/or aspects of the present invention, the polypeptide is selected from the group consisting of collagen, alginate, elastin, an elastin-like polypeptide, albumin, fibrin, chitosan, silk, poly(γ-glutamic acid) and polylysine.

According to some of any of the embodiments and/or aspects of the present invention, at least one of the layers of an elastic polymeric material comprises an electrospun polymeric material.

According to some of any of the embodiments and/or aspects of the present invention, the viscoelastic polymeric material comprises poly(lactic acid-co-ε-caprolactone).

According to some of any of the embodiments and/or aspects of the present invention, the viscoelastic polymeric material is characterized by a glass transition temperature and/or melting point at a temperature which is at least 5° C. lower than an ambient temperature of the composition-of-matter.

According to some of any of the embodiments and/or aspects of the present invention, the layer of a viscoelastic polymeric material is characterized by a storage shear modulus (G') in a range of from 0.01 to 10 MPa, at a temperature of 10° C. and frequency of 0.1 Hz.

According to some of any of the embodiments and/or aspects of the present invention, the layer of a viscoelastic polymeric material is characterized by a loss shear modulus in a range of from 0.0001 to 2 MPa, at a temperature of 10° C. and frequency of 0.1 Hz.

According to an aspect of some embodiments of the present invention there is provided a composition-of-matter comprising a multi-layer matrix, the matrix comprising at least one layer of an elastic polymeric material and at least one layer of a viscoelastic polymeric material, wherein the layer of a viscoelastic polymeric material is characterized by at least one of: a) a storage shear modulus (G') in a range of from 0.01 to 10 MPa, at a temperature of 10° C. and frequency of 0.1 Hz; b) a loss shear modulus (G") in a range of from 0.0001 to 2 MPa, at a temperature of 10° C. and frequency of 0.1 Hz; c) a glass transition temperature and/or melting point of the viscoelastic polymeric material which is at a temperature below 40° C.; and d) a loss tangent (G"/G') at a temperature of 10° C. and frequency of 0.1 Hz which is in a range of from 0.01 to 4, and wherein the layer of an elastic polymeric material is characterized by at least one of: a) an elastic modulus in a range of from 1 kPa to 1 GPa; b) an elongation at failure in a range of at least 100%; and c) a glass transition temperature and/or melting point of the elastic polymeric material which is at a temperature above 40° C.

According to an aspect of some embodiments of the present invention, there is provided a composition-of-matter comprising a multi-layer matrix, the matrix comprising at least one layer of an elastic electro spun polymeric material and at least one layer of a viscoelastic polymeric material, wherein: the elastic polymeric material is selected from the group consisting of poly(lactic acid-co-ε-caprolactone), poly(ε-caprolactone-co-L-lactic acid-co-glycolic acid-co-trimethylene carbonate), mixtures of poly(lactic acid-co-ε-caprolactone) and poly(lactic acid), and mixtures of poly(ε-caprolactone-co-L-lactic acid-co-glycolic acid-co-trimethylene carbonate) and poly(lactic acid), and the viscoelastic polymeric material is poly(lactic acid-co-ε-caprolactone).

According to some of any of the embodiments and/or aspects of the present invention, a matrix as described herein is characterized by a water-permeability of less than 1 ml per hour per cm$^2$ upon exposure to an aqueous liquid at a pressure of 40 mmHg.

According to an aspect of some embodiments of the present invention there is provided a layered matrix, characterized by a water-permeability of less than 1 ml per hour per cm$^2$ upon exposure to an aqueous liquid at a pressure of 40 mmHg.

According to some embodiments, the matrix is a layered matrix comprising at least one layer of an elastic polymeric material and at least one layer of a viscoelastic polymeric material.

According to some embodiments, the matrix is any one of the matrices described herein, in any one of the respective embodiments and any combination thereof.

According to some of any of the embodiments and/or aspects of the present invention, any of the compositions-of-matter described herein further comprises at least one additional ingredient, the additional ingredient being in a form of an additional layer on at least a portion of at least one surface of the matrix and/or dispersed within and/or on at least one surface of the matrix, the at least one additional ingredient imparting an additional functionality.

According to some embodiments of the present invention, the additional functionality is selected from the group consisting of water-impermeability, inhibition of formation of an adhesion to tissue, reduction of risk of infection, tissue rejection and/or immune response, and adhesion to tissue without suturing.

According to some embodiments of the present invention, the additional ingredient is selected from the group consisting of an adhesive material, a non-adhesive material, hydrophobic polymer particles, a biological and/or bio-active material, a growth factor, and a therapeutically effective agent.

According to some embodiments of the present invention, the additional layer is selected from the group consisting of a water-impermeable layer, a tissue-adhesive layer, a cell growth-promoting layer and an anti-fouling layer.

According to an aspect of some embodiments of the present invention there is provided a suturable and/or stapleable matrix capable of self-recovery, as defined herein. According to some embodiments, the matrix is any one of the matrices described herein, in any one of the respective embodiments and any combination thereof.

According to an aspect of some embodiments of the present invention there is provided an article-of-manufacture comprising any of the compositions-of-matter or matrices as described herein, in any one of the embodiments thereof and any combination of these embodiments.

According to some embodiments of the present invention, the article-of-manufacture of is a medical device, for example, an implantable medical device and/or a tissue substitute.

According to some of any of the embodiments of the present invention, the article-of-manufacture is identified for use in repairing tissue damage.

According to some embodiments of the present invention, the tissue is selected from the group consisting of dura mater, brain tissue, retina, skin tissue, hepatic tissue, pancreatic tissue, bone, cartilage, connective tissue, blood tissue, muscle tissue, cardiac tissue, vascular tissue, renal tissue, pulmonary tissue, gonadal tissue, hematopoietic tissue and fat tissue.

According to some of any of the embodiments of the present invention, the article-of-manufacture is identified for use in a treatment selected from the group consisting of dural repair, hernia repair, internal and/or topical wound closure, skin closure and/or repair, sealing tissues and/or organs in order to contain bodily fluids or air, sealing an anastomosis, inhibition of post-surgical adhesions between tissues, promotion of hemostasis, and administration of a therapeutically effective agent.

According to some of any of the embodiments of the present invention, the article-of-manufacture is for use in repairing and/or substituting a biological tissue.

According to an aspect of some embodiments of the present invention there is provided a method of repairing and/or substituting a biological tissue in a subject in need thereof, the method comprising contacting the biological tissue with the article-of-manufacture as described in any one of the embodiments thereof, thereby repairing and/or substituting the biological tissue.

According to some of any of the embodiments of the present invention, the biological tissue is a membrane.

According to some of any of the embodiments of the present invention, the membrane is dura mater.

According to some of any of the embodiments of the present invention, the biological tissue in any of the tissues described herein.

According to some of any of the embodiments of the present invention, the biological tissue the repairing and/or substituting a biological tissue comprises suturing and/or stapling the article-of-manufacture to the tissue.

According to an aspect of some embodiments of the present invention there is provided a process for preparing the composition-of-matter as described herein, the process comprising forming the layers of an elastic polymeric material and the at least one layer of a polymeric viscoelastic layer by continuous electrospinning.

According to an aspect of some embodiments of the present invention there is provided a process for preparing the composition-of-matter as described herein, the process comprising forming the layers of an elastic polymeric material by electrospinning, placing the at least one layer of a viscoelastic polymeric material parallel to the layers of an elastic polymeric material, and pressing the layers of an elastic polymeric material and the at least one layer of a viscoelastic polymeric material together, thereby forming the composition-of-matter.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings and images. With specific reference now to the drawings and images in detail, it is stressed that the particulars shown are by way of example and for purposes of illustrative discussion of embodiments of the invention. In this regard, the description taken with the drawings and images makes apparent to those skilled in the art how embodiments of the invention may be practiced.

In the drawings.

DESCRIPTION OF SPECIFIC EMBODIMENTS OF THE INVENTION

Figure 1:
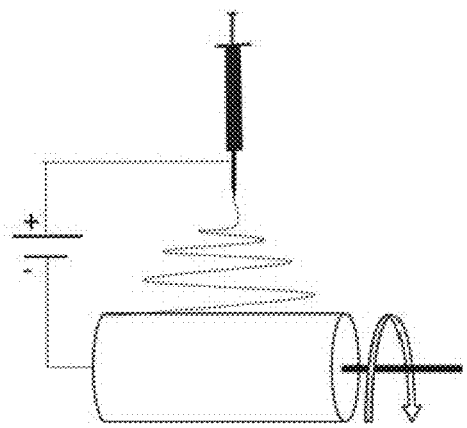
FIG. 1 is a scheme of an electrospinning apparatus for preparing electrospun materials according to some embodiments of the invention, showing a syringe filled with polymer solution placed at a fixed distance from an electrically grounded metal rotating collector, and a high-voltage DC generator connected to the needle of the syringe, for generating a strong electromagnetic field (over 5 kV) which draws fibers from the solution onto the collector; the polymer solution is driven out of the syringe at a steady rate by a syringe pump (not shown)

The present invention, in some embodiments thereof, relates to tissue substitutes, and more particularly, but not exclusively, to an elastic layered matrix and to uses thereof as a tissue substitute.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Current biocompatible matrices and technologies for tissue repair, such as dural substitutes, do not provide a desirable mechanical strength, flexibility and impermeability to biological fluids (such as cerebrospinal fluid) and pathogens. In particular, the widespread use of sutures and/or staples to hold a matrix in place can be particularly detrimental to the impermeability and mechanical strength and integrity of matrices, due to the formation of holes in the matrix.

The present inventors have uncovered matrices which can exhibit a desired degree of biocompatibility, mechanical strength, flexibility and/or impermeability, and furthermore, can respond to punctures such as those formed by suturing or stapling in a manner which limits the detrimental effects thereof.

Referring now to the drawings, FIG. 1 schematically depicts the formation of a layer of fibers by electrospinning. Elastic layers and/or viscoelastic layers may optionally be formed by such a technique.

Figure 2:
FIG. 2 is a scheme showing the structure of a 3-layer patch according to some embodiments of the invention.

FIG. 2 depicts a 3-layer patch according to some embodiments of the invention, wherein a viscoelastic layer is sandwiched between two elastic layers. FIGS. 3A-3D show exemplary elastic layers formed from electrospun fibers. FIGS. 4A, 4B, 5E, 5F and 6A-6C show exemplary 3-layer patches, wherein a viscoelastic layer is sandwiched between two elastic layers.

Figure 7:
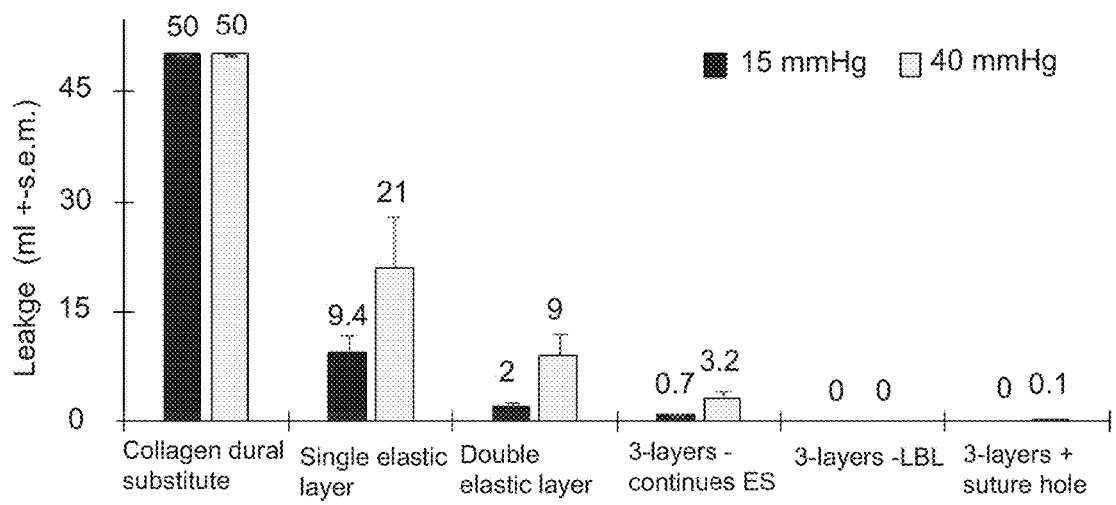
FIG. 7 is a bar graph showing the leakage of saline (mean volume±standard error of mean) over the course of 30 minutes at pressures of 15 or 40 mmHg through exemplary single layers, double elastic layers, and 3-layer patches prepared by continuous electrospinning (ES) or by pressing 3 sheets together (LBL), according to some embodiments of the invention, and 3-layer patches prepared by pressing 3 sheets together and containing a suture hole with suture in the hole, as well as leakage through collagen dural substitutes (for collagen dural substitutes, 50 ml of saline leaked through in less than 5 minutes)
Figure 8:
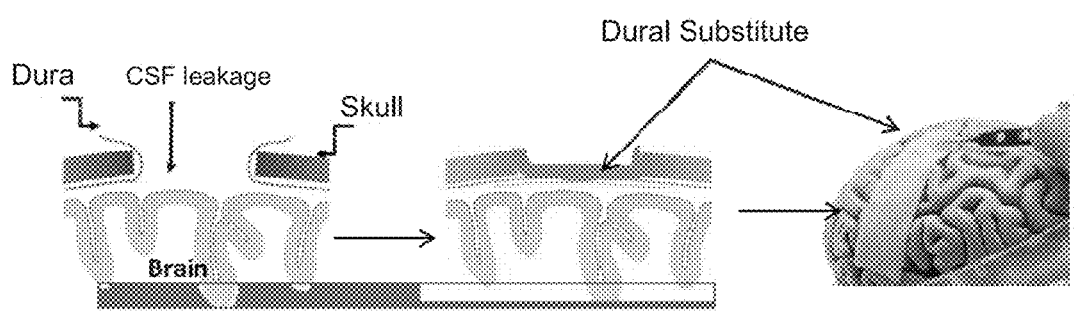
FIG. 8 (Background Art) is a scheme showing a breach in dura mater and skull before (left) and after (middle) closure of the breached dura mater with a commercially available dural substitute (thin green line) and closure of the breached skull (thick green line) (3-dimensional depiction of application of dural substitute on right).

FIGS. 5A-5D show that suture holes formed in an elastic layer of an exemplary 3-layer patch are effectively closed, in the presence or absence of the suture. FIG. 7 shows that exemplary 3-layer patches are highly water-impermeable, even when sutured, and that the viscoelastic layer contributes significantly to this water-impermeability.

Embodiments of the present invention relate to liquid-impermeable layered matrices which exhibit a unique combination of mechanical and rheological properties and to uses thereof in a variety of medical applications, and specifically, but not exclusively, as implants, and particularly as tissue substitutes such as, but not limited to, dura substitutes. Embodiments of the present invention further relate to recoverable matrices, which upon being subjected to suturing or stapling, self-recover so as to seal the holes formed by such procedures.

The layered matrices provided herein comprise two or layers, each made of a polymeric material, wherein one or more of these layers exhibit high elasticity and additional, one or more layers exhibit high viscoelasticity.

As exemplified herein, layered matrices such as described herein (also referred to herein as "patches") can be formed from biodegradable and biocompatible materials, while exhibiting considerable mechanical strength, a high degree of elasticity and flexibility, ease of handling, an ability to be folded (as may be useful for laparoscopic surgical procedures) without permanent deformation (e.g., without creasing), low density (which may decrease inflammation and infection), and a high degree of water-impermeability suitable for creating a tight seal, preventing fluid leakage, and preventing bacterial and viral infections.

The Matrix:

According to an aspect of some embodiments of the invention, there is provided a composition-of-matter comprising a multi-layer matrix, the matrix comprising one or more elastic layers and at least one viscoelastic layer. In some such embodiments, the matrix comprises at least two elastic layers. In exemplary embodiments, the matrix comprises two elastic layers and one viscoelastic layer interposed between the elastic layers.

As used herein, the term "composition-of-matter" includes a matrix which is also referred to herein interchangeably as a "core matrix", and may optionally further include additional components, ingredients and/or layers as described herein, according to any of the respective embodiments.

As used herein, the term "multi-layer" refers to a presence of at least two distinct layers. The distinct layers may differ, for example, in chemical composition, molecular configuration (e.g., degree and type of crystallinity), physical structure and/or mechanical properties.

Herein, the term "matrix" (including "core matrix"), when used in the context of a composition-of-matter comprising a multi-layer matrix as described herein, refers to the one or more elastic layers and viscoelastic layers (as described herein, according to any of the respective embodiments) and further includes any materials incorporated within and/or interposed between the elastic and/or viscoelastic layers. That is, the matrix does not include any component of the composition-of-matter which is outside of (i.e., neither within nor between) the elastic and viscoelastic layers.

In some embodiments of any one of the embodiments described herein, the matrix is defined by elastic layers (as described herein, according to any of the respective embodiments) and includes any materials (including, but not limited to, a viscoelastic layer according to any of the respective embodiments described herein) incorporated within and/or interposed between the elastic layers. That is, the core matrix does not include any component of the composition-of-matter which is outside of the elastic layers.

As used herein, the phrase "elastic layer" refers to a layer of material, wherein the layer exhibits elasticity.

Herein, the terms "elasticity" and "elastic" refer to a tendency of a material (optionally in a form of a layer) to return to its original shape after being deformed by stress, for example, a tensile stress and/or shear stress, at an indicated temperature or at a temperature of 37° C. (in contexts wherein no temperature is indicated).

As used herein, the phrase "viscoelastic layer" refers to a layer of material, wherein the layer exhibits viscoelasticity.

Herein, the terms "viscoelasticity" and "viscoelastic" refer to a tendency of a material (optionally in a form of a layer) to resist stress to a degree which correlates with the rate of deformation (e.g., strain, shear), at an indicated temperature or at a temperature of 37° C. (in contexts wherein no temperature is indicated). That is, when deformation is effected relatively slowly, the resistance of the material is lower (e.g., due to viscous flow during deformation), and the resistance may optionally approach zero as the rate of deformation (e.g., shear) approaches zero. The resistance will typically not be sufficient to allow the material to return to its original shape, except in some cases wherein the rate of deformation is very high.

A degree of viscoelasticity may optionally be characterized by a loss tangent (G"/G'), which is a ratio of a loss shear modulus (G", also referred to herein interchangeably as a "shear loss modulus") to storage shear modulus (G', also referred to herein interchangeably as a "shear storage modulus"). A loss shear modulus reflects viscous behavior, whereas a storage shear modulus reflects elastic behavior.

In some embodiments, of any one of the embodiments described herein, a viscoelastic material (e.g., viscoelastic layer) is characterized in that a loss tangent of at least 0.01.

In some embodiments, of any one of the embodiments described herein, the viscoelastic layer is characterized by a loss tangent which is greater than a loss tangent of the elastic layer. In some embodiments, a viscoelastic layer is characterized by a loss tangent which is at least 200% of (two-fold) a loss tangent of the elastic layer.

Storage shear modulus and loss shear modulus may optionally be determined using a shear rheometer, for example, a strain-controlled rotational rheometer, at an indicated temperature and frequency (e.g., using procedures described in the Examples section herein).

The elastic and viscoelastic layers described herein are preferably made of a polymeric material selected to exhibit the elasticity and/or viscoelasticity according to any of the respective embodiments described herein. A person skilled in the art would recognize which polymeric materials (e.g., polymers and mixtures thereof) to select, and how to produce a layer therefrom in order to obtain a layer exhibiting the indicated features (e.g., elasticity and/or viscoelasticity) without undue experimentation, particularly in view of the description and guidance provided herein.

Herein, in embodiments wherein an elastic layer is made of a polymeric material, the phrase "elastic layer" and "layer of an elastic polymeric material" are used interchangeably.

Herein, in embodiments wherein a viscoelastic layer is made of a polymeric material, the phrase "viscoelastic layer" and "layer of a viscoelastic polymeric material" are used interchangeably.

In some embodiments of any one of the embodiments described herein, the matrix contains one layer of viscoelastic material.

The elastic layer(s) and viscoelastic layer(s) may be layered in any order. An elastic layer may optionally be adjacent to (e.g., in direct contact with) a viscoelastic layer and/or another elastic layer, and a viscoelastic layer may optionally be adjacent to (e.g., in direct contact with) an elastic layer and/or another viscoelastic layer. In some embodiments of any one of the embodiments described herein, the matrix comprises at least one viscoelastic layer between the elastic layers (according to any of the respective embodiments described herein). Such a configuration includes, for example, more than one viscoelastic layer between a pair of elastic layers, and one or more elastic layers which, along with the viscoelastic layer(s), are interposed between other elastic layers.

As used herein, a material (e.g., viscoelastic layer) which is "between" layers (e.g., elastic layers) is located in at least a portion of the region between the layers, and does not exclude other substances from also being between the layers, and optionally is not in contact with one or more of the layers.

Without being bound by any particular theory, it is believed that a location of a viscoelastic polymeric material between elastic layers, allows the elastic layers to contain the viscoelastic polymeric material within the matrix, and prevent significant leaching of the viscoelastic polymeric material. It is further believed that a viscoelastic polymeric material is in a form of an intermediate layer is highly suitable for acting as a barrier and for closing holes, as described herein, while being effectively contained by the elastic layers.

In some embodiments of any one of the embodiments described herein, the core matrix contains two elastic layers as described herein (according to any of the respective embodiments) and one viscoelastic layer as described herein (according to any of the respective embodiments) interposed between the two elastic layers.

Herein, the term "polymeric material" (including within the phrases "elastic polymeric material" and "viscoelastic polymeric material") refer to a material comprising one or more polymers (as defined herein), wherein at least 20 weight percents (by dry weight) of the material consists of the one or more polymers.

In some embodiments of any of the embodiments described herein, at least 30 weight percents (by dry weight) of the polymeric material (e.g., elastic polymeric material and/or viscoelastic polymeric material) consists of one or more polymers. In some embodiments, at least 40 weight percents (by dry weight) of the polymeric material consists of one or more polymers. In some embodiments, at least 50 weight percents (by dry weight) of the polymeric material consists of one or more polymers. In some embodiments, at least 60 weight percents (by dry weight) of the polymeric material consists of one or more polymers. In some embodiments, at least 70 weight percents (by dry weight) of the polymeric material consists of one or more polymers. In some embodiments, at least 80 weight percents (by dry weight) of the polymeric material consists of one or more polymers. In some embodiments, at least 90 weight percents (by dry weight) of the polymeric material consists of one or more polymers. In some embodiments, the polymeric material (e.g., elastic polymeric material and/or viscoelastic polymeric material) consists essentially of one or more polymers.

The term "polymer", as used herein, encompasses organic and inorganic polymer and further encompasses one or more of a polymer, a copolymer or a mixture thereof (a blend). Polymers used in embodiments of the invention may be synthetic and/or natural (e.g., biological) in origin.

Non-limiting examples of polymers which are suitable for use in elastic and/or viscoelastic polymeric materials described herein include homo-polymers and co-polymers such as polyesters (e.g., poly(ethylene terephthalate) and aliphatic polyesters made of glycolide (glycolic acid), lactide (lactic acid, including L-lactic acid and/or D-lactic acid), ε-caprolactone, dioxanone (e.g., p-dioxanone), trimethylene carbonate, hydroxybutyrate and/or hydroxyvalerate); polypeptides made of natural and/or modified amino acids (e.g., collagen, alginate, elastin, elastin-like polypeptides, albumin, fibrin, chitosan, silk, poly(γ-glutamic acid) and polylysine); polyethers, such as synthetic polyethers (e.g., poly(ethylene glycol)); polysaccharides made of natural and/or modified saccharides (e.g., hyaluronic acid); polydepsipeptides; biodegradable nylon co-polyamides; polydihydropyrans; polyphosphazenes; poly(orthoesters); poly(cyanoacrylates); polyanhydrides; polyurethanes; polycarbonates; silicones; polyamides (e.g., nylons); polysulfones; polyether ether ketones (PEEKs); polytetrafluoroethylene; polyethylene; and polyacrylate esters (e.g., poly (methyl methacrylate), poly(ethyl methacrylate), poly (methyl acrylate) and poly(ethyl acrylate)); any copolymer thereof (including any ratio of the respective monomers) and any combination thereof.

While any polymer, copolymer or a mixture of polymers and/or copolymers can be used for producing the elastic and/or viscoelastic polymeric material described herein, according to some embodiments of any one of the embodiments described herein relating to elastic and/or viscoelastic polymeric material, the elastic and/or viscoelastic polymeric material is formed of a biocompatible and/or biodegradable polymer.

In some embodiments, the elastic polymeric material, fibers formed from the elastic polymeric material and/or viscoelastic polymeric material described herein are biocompatible and biodegradable.

In some embodiments, the elastic polymeric material, fibers formed from the elastic polymeric material and/or viscoelastic polymeric material described herein are biocompatible and non-biodegradable.

As used herein, the term "biocompatible" refers to a material which the skilled practitioner would expect the body to generally accept without significant toxicity, immune response and/or rejection, or excessive fibrosis. In some embodiments, a moderate degree of immune response and/or fibrosis may optionally be acceptable or desired.

The term "biodegradable" as used in the context of the present invention, describes a material which can decompose under physiological and/or environmental conditions into breakdown products. Such physiological and/or environmental conditions include, for example, hydrolysis (decomposition via hydrolytic cleavage), enzymatic catalysis (enzymatic degradation), and mechanical interactions. This term typically refers to substances that decompose under these conditions such that 30 weight percent of the substance decompose within a time period shorter than one year.

The term "biodegradable" as used in the context of the present invention, also encompasses the term "bioresorbable", which describes a substance that decomposes under physiological conditions to break down to products that undergo bioresorption into the host-organism, namely, become metabolites of the biochemical systems of the host-organism.

It is expected that during the life of a patent maturing from this application many relevant biocompatible and/or biodegradable polymers will be developed and the scope of the terms "biocompatible" and "biodegradable" is intended to include all such new technologies a priori.

Preferred biodegradable polymers according to the present embodiments are non-toxic and benign biocompatible polymers. In some such embodiments, the biodegradable polymer is a bioresorbable polymers which decomposes into non-toxic and benign breakdown products that are absorbed in the biochemical systems of the subject.

Non-limiting examples of biodegradable polymers which are suitable for use in elastic and/or viscoelastic polymeric materials described herein include homo-polymers and co-polymers such as aliphatic polyesters made of glycolide (glycolic acid), lactide (lactic acid, including L-lactic acid and/or D-lactic acid), ε-caprolactone, dioxanone (e.g., p-dioxanone), trimethylene carbonate, hydroxybutyrate and/or hydroxyvalerate; polypeptides made of natural and/or modified amino acids (e.g., collagen, alginate, elastin, elastin-like polypeptides, albumin, fibrin, chitosan, silk, poly(γ-glutamic acid) and polylysine); polysaccharides made of natural and/or modified saccharides (e.g., hyaluronic acid); polydepsipeptides; biodegradable nylon co-polyamides; polydihydropyrans; polyphosphazenes; poly(orthoesters); poly(cyanoacrylates); polyanhydrides; copolymers thereof (including any ratio of the respective monomers); and any combination thereof.

Non-limiting examples of non-biodegradable polymers which are suitable for use in elastic and/or viscoelastic polymeric materials described herein include polyurethanes, polycarbonates, silicones, polyamides (e.g., nylons), polysulfones, polyether ether ketones (PEEKs), polytetrafluoroethylene, polyethylene, poly(methyl methacrylate), poly(ethyl methacrylate), poly(methyl acrylate), poly(ethyl acrylate) and non-biodegradable polyesters such as, for example, poly(ethylene terephthalate).

In some embodiments of any one of the embodiments described herein, any one or more of the elastic and viscoelastic layers is made of polymer fibers. In some embodiments, the fibers are electrospun fibers.

The term "fiber", as used herein, describes a class of structural elements, similar to pieces of thread, that are made of continuous filaments and/or discrete elongated pieces.

In some embodiments of any one of the embodiments described herein, the matrix has a sheet-like geometry. In some embodiments, both the composition-of-matter and the matrix have a sheet-like geometry.

In some embodiments of any one of the embodiments described herein, the sheet-like geometry is characterized in that a mean thickness in one dimension (e.g., a mean width in the dimension in which the matrix is narrowest) is less than 20% of a mean width in each of two perpendicular dimensions. In some such embodiments, a mean thickness in one dimension is less than 10% of a mean width in each of two perpendicular dimensions. In some such embodiments, a mean thickness in one dimension is less than 5% of a mean width in each of two perpendicular dimensions. In some such embodiments, a mean thickness in one dimension is less than 2% of a mean width in each of two perpendicular dimensions. In some such embodiments, a mean thickness in one dimension is less than 1% of a mean width in each of two perpendicular dimensions. In some such embodiments, a mean thickness in one dimension is less than 0.5% of a mean width in each of two perpendicular dimensions. In some such embodiments, a mean thickness in one dimension is less than 0.2% of a mean width in each of two perpendicular dimensions. In some such embodiments, a mean thickness in one dimension is less than 0.1% of a mean width in each of two perpendicular dimensions.

In some embodiments of any one of the embodiments described herein, the matrix is characterized by a mean thickness of less than 3 mm (e.g., between 60 μm and 3 mm). In some such embodiments, the mean thickness is less than 2 mm (e.g., between 60 μm and 2 mm). In some such embodiments, the mean thickness is less than 1.5 mm (e.g., between 60 μm and 1.5 mm). In some such embodiments, the mean thickness is less than 1.25 mm (e.g., between 60 μm and 1.25 mm). In some such embodiments, the mean thickness is less than 1 mm (e.g., between 60 μm and 1 mm). In some such embodiments, the mean thickness is less than 750 μm (e.g., between 60 and 750 μm). In some such embodiments, the mean thickness is less than 500 μm (e.g., between 60 and 500 μm). In some such embodiments, the mean thickness is less than 250 μm (e.g., between 60 and 250 μm).

In some embodiments of any one of the embodiments described herein, a mean total thickness of the elastic layers is at least 50% (e.g., from 50 to 99%) of the mean thickness of the matrix. In some such embodiments, a mean total thickness of the elastic layers is at least 60% (e.g., from 60 to 99%) of the mean thickness of the matrix. In some such embodiments, a mean total thickness of the elastic layers is at least 70% (e.g., from 70 to 99%) of the mean thickness of the matrix. In some such embodiments, a mean total thickness of the elastic layers is at least 80% (e.g., from 80 to 99%) of the mean thickness of the matrix. In some such embodiments, a mean total thickness of the elastic layers is at least 90% (e.g., from 90 to 99%) of the mean thickness of the matrix.

As exemplified in the Examples section herein, multilayer matrices as described herein exhibit a considerably degree of water-impermeability.

In some embodiments of any one of the embodiments described herein, the matrix is characterized by a water-permeability of less than 1 ml per hour per $cm^2$ upon exposure to an aqueous liquid at a pressure of 40 mmHg. In some such embodiments, the water-permeability is less than 0.3 ml per hour per $cm^2$. In some embodiments, the water-permeability is less than 0.1 ml per hour per $cm^2$. In some embodiments, the water-permeability is less than 0.03 ml per hour per $cm^2$. In some embodiments, the water-permeability is less than 0.01 ml per hour per $cm^2$.

In some embodiments of any one of the embodiments described herein, the matrix is characterized by a water-permeability of less than 1 ml per hour per $cm^2$ upon exposure to an aqueous liquid at a pressure of 15 mmHg. In some such embodiments, the water-permeability is less than 0.3 ml per hour per $cm^2$. In some embodiments, the water-permeability is less than 0.1 ml per hour per $cm^2$. In some embodiments, the water-permeability is less than 0.03 ml per hour per $cm^2$. In some embodiments, the water-permeability is less than 0.01 ml per hour per $cm^2$.

Herein, water-permeability is determined in accordance with ISO 811, according to procedures as described in the Examples section below. The matrix is placed at the bottom of a column of aqueous liquid (optionally water, and optionally phosphate buffer saline) having a height which provides the indicated pressure, at 37° C. The area of the matrix exposed to the liquid is optionally about 9 $cm^2$. The amount of aqueous liquid which passes the matrix during the course of a given period of time (optionally 30 minutes), when divided by the period of time and the area exposed to the liquid, determines the water-permeability.

In some embodiments of any one of the embodiments described herein, the composition-of-matter further comprising at least one additional ingredient (also referred to herein as "additive") which imparts an additional functionality.

In some such embodiments, the additional ingredient(s) is in a form of at least one additional layer. The additional layer(s) is optionally on at least a portion of at least one surface of the core matrix and/or within the core matrix (e.g., between two other layers of the core matrix, as described herein).

Alternatively or additionally, in some embodiments, the additional ingredient(s) is dispersed within the core matrix and/or present on at least one surface, or a portion thereof, of the matrix.

Except where indicated otherwise, an additional ingredient is considered herein as part of the matrix when present within the core matrix, but not when present outside the matrix (e.g., on a surface or a portion of a surface of the matrix).

Examples of additional functionalities which may be imparted by an additional ingredient include, without limitation, water-impermeability, which may optionally be provided by an additive in a form of a water-impermeable layer and/or by a hydrophobic additive); inhibition of formation of an adhesion to tissue, which may be optionally be provided by an additive characterized by reduced adhesion to tissue, and/or by an agent which inhibits cell growth; reduction of risk of infection, which may optionally be provided by an antimicrobial agent, such as an antibiotic, and/or by a film which inhibits penetration of pathogens; reduction of risk of tissue rejection and/or immune response, which may optionally be provided by an agent which modulates an immune system; and adhesion to tissue without suturing, which may optionally be provided by an adhesive (e.g., applied on a surface) and/or an agent and/or surface which promotes cell growth and/or attachment (e.g., growth factors, extracellular matrix proteins, and/or other proteins). Examples of layers which may be formed from additional ingredients which impart such functionalities include, without limitation, water-impermeable layers, tissue-adhesive layers (i.e., layers characterized by enhanced adherence to cells, as compared with the core matrix without a tissue-adhesive layer), cell growth-promoting layers and anti-fouling layers (i.e., layers characterized by reduced adherence to cells, as compared with the core matrix without an anti-fouling layer).

Examples of additional ingredients which may be included in the composition-of-matter ingredient include, without limitation, adhesive materials, non-adhesive materials (e.g., materials characterize by particularly low adherence to tissue and/or other substrate), hydrophobic polymer particles, biological and/or bio-active materials, cellular components (e.g., a cell signaling protein, an extracellular matrix protein, a cell adhesion protein, a growth factor, protein A, a protease and a protease substrate), growth factors and therapeutically active agents.

Additional ingredients (e.g., therapeutically active agents) which can be beneficially incorporated into the composition-of-matter include both natural or synthetic polymeric (macro-biomolecules, for example, proteins, enzymes) and non-polymeric (small molecule therapeutics) natural or synthetic agents.

Examples of suitable therapeutically active agents include, without limitation, anti-proliferative agents, cytotoxic factors or cell cycle inhibitors, including CD inhibitors, such as p53, thymidine kinase ("TK") and other agents useful for interfering with cell proliferation.

Examples of therapeutically active agents that inhibit cell proliferation and/or angiogenesis (antiproliferative drugs) which are particularly useful in drug-eluting systems destined for anticancer treatment, include paclitaxel, sirolimus (rapamycin), farnesylthiosalicylate (FTS, salirasib), fluoro-FTS, everolimus, zotarolimus, daunorubicin, doxorubicin, N-(5,5-diacetoxypentyl)doxorubicin, anthracycline, mitomycin C, mitomycin A, 9-amino camptothecin, aminopertin, antinomycin, $N^8$-acetyl spermidine, 1-(2-chloroethyl)-1,2-dimethanesulfonyl hydrazine, bleomycin, tallysomucin, etoposide, camptothecin, irinotecan, topotecan, 9-amino camptothecin, paclitaxel, docetaxel, esperamycin, 1,8-dihydroxy-bicyclo[7.3.1]trideca-4-ene-2,6-diyne-13-one, anguidine, morpholino-doxorubicin, vincristine, vinblastine and derivatives thereof.

Additional therapeutically active agents which can be beneficially incorporated into the composition-of-matter include antibiotic agents. Non-limiting examples of suitable antibiotic agents include gentamicin, ceftazidime, mafenide benzoyl peroxide, octopirox, erythromycin, zinc, silver, tetracyclin, triclosan, azelaic acid and its derivatives, phenoxyethanol and phenoxypropanol, ethyl acetate, clindamycin and meclocycline; sebostats such as flavinoids; alpha and beta hydroxy acids; polydiallyldimethylammonium chloride and bile salts such as scymnol sulfate and its derivatives, deoxycholate and cholate.

Additional therapeutically active agents which can be beneficially incorporated into the composition-of-matter include analgesic agents, anaesthetic agents, pain-killers, pain-reducers and the like (including NSAIDs, COX-2 inhibitors, K+ channel openers, opiates and morphinomimetics); and hemostatic agents and antihemorrhagic agents.

According to an aspect of some embodiments of the invention, there is provided a suturable and/or stapleable matrix capable of self-recovery.

Herein, the term "suturable" refers to an ability to have a needle pass through the matrix without causing a rupture (e.g., a crack or tear) in the matrix other than a localized hole similar in area to the needle cross-section.

Herein, the term "stapleable" refers to an ability to have a staple pass through the matrix without causing a rupture (e.g., a crack or tear) in the matrix other than a localized hole similar in area to the staple cross-section.

The needle and staple in the above definitions of "suturable" and "stapleable" have a cross-section (optionally, a circular cross-section) of no more than 1 mm$^2$. Optionally, the needle is a 21-gauge needle (diameter ~0.51 mm).

Herein, the term "self-recover" refers to an ability of a material (e.g., material in the matrix) to at least partially close a hole formed in the material (optionally by a 21-gauge needle) by movement of a portion of the material into the space of the hole (e.g., by elastic rebound and/or plastic deformation), such that a hole remaining in the material the needle (if any) is less than 50% of an area of a cross-section of the object which formed the hole (e.g., optionally by a 21-gauge needle).

According to an aspect of some embodiments of the invention there is provided a multi-layer matrix comprising at least one layer of an elastic polymeric material (e.g., according to any one of the respective embodiments described herein) and at least one layer of a viscoelastic polymeric material (e.g., according to any one of the respective embodiments described herein), the matrix being characterized by a water-permeability of less than 1 ml per hour per cm$^2$ upon exposure to an aqueous liquid at a pressure of 40 mmHg (as defined herein). In some such embodiments, the matrix is a suturable matrix capable of self-recovery (e.g., according to any one of the respective embodiments described herein). Additionally, some embodiments of any of the embodiments described herein which relate to a matrix exhibit the aforementioned water-permeability.

In some embodiments of any one of the embodiments described herein, a matrix according to an of the aspects described herein exhibits a suture retention ability characterized in that a minimum mean force applied to a suture in the matrix which is sufficient to cause failure of the matrix is at least 100 grams force, and optionally at least 200 grams force.

Suture retention is tested based on the method described in the ANSI/AAMI/ISO 7198:1998/2001/(R) 2004 standard, as described in the Examples section below. The matrix is sutured with a single 4/0 suture (e.g., Premilene® 4/0 suture) at a minimum distance of 2 mm from its free end, and a tensile test is conducted (e.g., as described herein) in order to measure the force at failure of the matrix.

The Elastic Layer:

An elastic layer according to any one of the embodiments described in this section described in this section may be combined with a viscoelastic polymeric material and/or viscoelastic layer according to any one of the respective embodiments described herein.

In some embodiments of any one of the embodiments described herein, the elastic layer is a porous layer.

Herein, the phrase "porous layer" refers to a layer which comprises voids (e.g., in addition to polymeric material described herein), for example, the space between the polymeric material is not filled in by an additional substance. However, porous layers may optionally comprise an additional substance in the spaces between the polymeric material, provided that at least a portion of the volume of the voids is not filled in by the additional substance.

Porous layers may be, for example, in a form of fibers (e.g., woven or non-woven fibers, a foam and/or a sponge. Many suitable techniques will be known to the skilled practitioner for preparing a polymeric material in porous form, including, without limitation, various techniques for spinning fibers, use of a gas to form a foam, and drying (e.g., lyophilizing) a suspension of polymeric material.

In some embodiments of any one of the embodiments described herein relating to one or more porous layers (e.g., porous elastic layers), the porous layers are characterized by a porosity of at least 50% (e.g., from 50 to 99%). In some such embodiments, the porous layers are characterized by a porosity of at least 60% (e.g., from 60 to 99%). In some such embodiments, the porous layers are characterized by a porosity of at least 70% (e.g., from 70 to 99%). In some such embodiments, the porous layers are characterized by a porosity of at least 80% (e.g., from 80 to 99%). In some such embodiments, the porous layers are characterized by a porosity of at least 90% (e.g., from 90 to 99%). In some such embodiments, the porous layers are characterized by a porosity of about 90%.

As shown in the Examples section herein, the present inventors have surprisingly uncovered that even a highly porous elastic layer reduces matrix water-permeability considerably.

Herein, the term "porosity" refers to a percentage of the volume of a substance (e.g., an elastic polymeric material described herein) which consists of voids.

In some embodiments of any one of the embodiments described herein, one or more elastic layers (e.g., porous elastic layers, according to any of the respective embodiments described herein) are independently made of polymeric fibers.

Without being bound by any particular theory, it is believed that a fibrous structure of an elastic layer made of polymeric fibers advantageously allows a needle to pass through the layer by pushing fibers aside without any considerable amount of permanent deformation or mechanical disruption of the layers, and that the elasticity of the fibers causes the layers to rebound, thereby closing suture holes and holding tightly to sutures.

In some embodiments of any one of the embodiments described herein, the fibers are polymeric fibers.

The fibers which form the elastic layers may be woven or non-woven. In some embodiments of any one of the embodiments described herein, the fibers are non-woven.

In some embodiments of any one of the embodiments described herein, the fibers in the elastic layer(s) are electrospun.

Without being bound by any particular theory, it is believed that electrospun fibers, and structurally similar fibers, are particularly suitable for forming elastic layers such as described herein. In particular, layers of electrospun fibers can be prepared from a wide variety of materials, and allow control over pore size, fiber size, fiber alignment, hydrophobicity, elasticity and mechanical strength.

In some embodiments of any one of the embodiments described herein relating to polymeric fibers, at least 20 weight percents (by dry weight) of the polymeric fiber consists of one or more polymers. In some embodiments, at least 30 weight percents (by dry weight) of the polymeric fiber consists of one or more polymers. In some embodiments, at least 40 weight percents (by dry weight) of the polymeric fiber consists of one or more polymers. In some embodiments, at least 50 weight percents (by dry weight) of the polymeric fiber consists of one or more polymers. In some embodiments, at least 60 weight percents (by dry weight) of the polymeric fiber consists of one or more polymers. In some embodiments, at least 70 weight percents (by dry weight) of the polymeric fiber consists of one or more polymers. In some embodiments, at least 80 weight percents (by dry weight) of the polymeric fiber consists of one or more polymers. In some embodiments, at least 90 weight percents (by dry weight) of the polymeric fiber consists of one or more polymers. In some embodiments, the polymeric fiber consists essentially of one or more polymers.

In some embodiments of any one of the embodiments described herein, the fibers (e.g., polymeric fibers according to any of the respective embodiments described herein) in at least one of the porous layers of fibers (according to any one of the respective embodiments described herein) are characterized by a mean diameter in a range of from 0.001 to 30 $\mu m$. In some such embodiments, the mean diameter is in a range of from 0.003 to 30 $\mu m$. In some such embodiments, the mean diameter is in a range of from 0.01 to 30 $\mu m$. In some such embodiments, the mean diameter is in a range of from 0.03 to 30 $\mu m$. In some such embodiments, the mean diameter is in a range of from 0.1 to 30 $\mu m$. In some such embodiments, the mean diameter is in a range of from 0.3 to 30 $\mu m$. In some such embodiments, the mean diameter is in a range of from 1 to 10 $\mu m$. In some such embodiments, the mean diameter is in a range of from 1 to 4 $\mu m$. In some such embodiments, the mean diameter is about 3 $\mu m$.

In some embodiments of any one of the embodiments described herein, the fibers (e.g., polymeric fibers according to any of the respective embodiments described herein) in each of the porous layers of fibers (according to any one of the respective embodiments described herein) are characterized by a mean diameter in a range of from 0.001 to 30 $\mu m$. In some such embodiments, the mean diameter is in a range of from 0.003 to 30 $\mu m$. In some such embodiments, the mean diameter is in a range of from 0.01 to 30 $\mu m$. In some such embodiments, the mean diameter is in a range of from 0.03 to 30 $\mu m$. In some such embodiments, the mean diameter is in a range of from 0.1 to 30 $\mu m$. In some such embodiments, the mean diameter is in a range of from 0.3 to 30 $\mu m$. In some such embodiments, the mean diameter is in a range of from 1 to 10 $\mu m$. In some such embodiments, the mean diameter is in a range of from 1 to 4 $\mu m$. In some such embodiments, the mean diameter is about 3 $\mu m$.

In some embodiments of any one of the embodiments described herein, the fibers in at least one of the porous layers of fibers (according to any one of the respective embodiments described herein) are characterized by a mean diameter in a range of from 0.001 to 10 $\mu m$. In some such embodiments, the mean diameter is in a range of from 0.3 to 3 µm. In some such embodiments, the mean diameter is in a range of from 0.3 to 1 µm.

In some embodiments of any one of the embodiments described herein, the fibers in each of the porous layers of fibers (according to any one of the respective embodiments described herein) are characterized by a mean diameter in a range of from 0.3 to 10 µm. In some such embodiments, the mean diameter is in a range of from 0.3 to 3 µm. In some such embodiments, the mean diameter is in a range of from 0.3 to 1 µm.

In some embodiments of any one of the embodiments described herein, the fibers in at least one of the porous layers of fibers (according to any one of the respective embodiments described herein) are characterized by a mean diameter in a range of from 1 to 30 µm. In some such embodiments, the mean diameter is in a range of from 3 to 30 µm. In some such embodiments, the mean diameter is in a range of from 10 to 30 µm.

In some embodiments of any one of the embodiments described herein, the fibers in each of the porous layers of fibers (according to any one of the respective embodiments described herein) are characterized by a mean diameter in a range of from 1 to 30 µm. In some such embodiments, the mean diameter is in a range of from 3 to 30 µm. In some such embodiments, the mean diameter is in a range of from 10 to 30 µm.

In some embodiments of any one of the embodiments described herein, at least one of the elastic layers (according to any one of the respective embodiments described herein) is characterized by a mean thickness in a range of from 10 to 500 µm. In some such embodiments, the mean thickness is in a range of from 25 to 350 µm. In some such embodiments, the mean thickness is in a range of from 50 to 250 µm.

In some embodiments of any one of the embodiments described herein, each of the elastic layers (according to any one of the respective embodiments described herein) is characterized by a mean thickness in a range of from 10 to 500 µm. In some such embodiments, the mean thickness is in a range of from 25 to 350 µm. In some such embodiments, the mean thickness is in a range of from 50 to 250 µm.

In some embodiments of any one of the embodiments described herein, at least one elastic layer according to any of the respective embodiments described herein is characterized by at least one of the following 3 properties:

a) an elastic modulus (Young's modulus) in a range of from 1 kPa to 1 GPa;

b) an elongation at failure of at least 100% (e.g., in a range of from 100% to 1000%); and c) a glass transition temperature and/or melting point of said elastic polymeric material which is at a temperature above 40° C.

Herein throughout, the phrase "elastic modulus" refers to Young's modulus, as determined by response of a material to application of tensile stress (e.g., according to procedures described in the Examples section herein).

Tensile properties described herein (e.g., elastic modulus, elongation at failure, recovery and ultimate tensile strength) are determined in accordance with ASTM international standard D882-12 for testing tensile properties of thin plastic sheeting. Except where indicated otherwise, the tensile properties are determined after the layers are immersed in aqueous liquid (e.g., water, phosphate buffer saline), and at a temperature of 37° C. (e.g., according to procedures described in the Examples section herein). Tensile testing characterizes an amount of tensile stress applied to the tested material as a function of tensile strain (increase in length due to tensile stress, as a percentage of the original length) of the material.

The ultimate tensile strength is determined as the maximal stress which can be applied to the tested material, such that any further strain is obtained with reduced stress (a phenomenon known as "necking" or is unobtainable because the tensile stress results in rupture (e.g., tearing, cracking) of the material.

The elongation at failure is determined as the maximal strain (elongation) which can occur (upon application of tensile stress equal to the ultimate tensile strength) before failure of the tested material occurs (e.g., as rupture or necking).

The elastic modulus is determined as the gradient of stress as a function of strain over ranges of stress and strain wherein stress is a linear function of strain (e.g., from a stress and strain of zero, to the elastic proportionality limit, and optionally from zero strain to a strain which is no more than 50% of the elongation at failure).

Recovery is determined by releasing the tensile stress after subjecting the tested material as the ratio of the decrease in length to a prior strain after a material (e.g., elastic layer) is subjected to a prior strain which is almost equal to the elongation at failure (optionally about 90% of the elongation at failure, optionally about 95% of the elongation at failure, optionally about 98% of the elongation at failure, optionally about 99% of the elongation at failure, wherein the elongation at failure can be determined using an equivalent sample). Thus, for example, a material extended to an elongation at failure which is 200%, and which upon release of tensile stress returns to a state characterized by a strain of 20% relative to the original length, would be characterized as having a recovery of 90% (i.e., 200%-20% divided by 200%).

In some embodiments of any one of the embodiments described herein, each of the elastic layers in a matrix according to any of the respective embodiments described herein is characterized by at least one of the abovementioned 3 properties.

In some embodiments of any one of the embodiments described herein, at least one elastic layer (according to any of the respective embodiments described herein) is characterized by at least two of the abovementioned 3 properties. In some such embodiments, each of the elastic layers in a matrix (according to any of the respective embodiments described herein) is characterized by at least two of the abovementioned 3 properties.

In some embodiments of any one of the embodiments described herein, at least one elastic layer (according to any of the respective embodiments described herein) is characterized by each of the abovementioned 3 properties. In some such embodiments, each of the elastic layers in a matrix (according to any of the respective embodiments described herein) is characterized by each of the abovementioned 3 properties.

In some embodiments of any one of the embodiments described herein, at least one elastic layer is characterized by a recovery of at least 75% (e.g., from 75 to 99.9%). In some such embodiments, the recovery is at least 80% (e.g., from 80 to 99.9%). In some such embodiments, the recovery is at least 85% (e.g., from 85 to 99.9%). In some such embodiments, the recovery is at least 90% (e.g., from 90 to 99.9%). In some such embodiments, the recovery is at least 95% (e.g., from 95 to 99.9%).

In some embodiments of any one of the embodiments described herein, at least one elastic layer is characterized by an elastic modulus (Young's modulus) in a range of from 1 kPa to 1 GPa. In some such embodiments, the elastic modulus is in a range of from 3 kPa to 500 MPa. In some such embodiments, the elastic modulus is in a range of from 10 kPa to 200 MPa. In some such embodiments, the elastic modulus is in a range of from 20 kPa to 100 MPa. In some such embodiments, the elastic modulus is in a range of from 50 kPa to 50 MPa. In some such embodiments, the elastic modulus is in a range of from 50 kPa to 20 MPa. In some such embodiments, the elastic modulus is in a range of from 50 kPa to 10 MPa. In some such embodiments, the elastic modulus is in a range of from 100 kPa to 3 MPa. In some such embodiments, each of the elastic layers in a matrix (according to any of the respective embodiments described herein) is characterized by an elastic modulus in a range according to any of the aforementioned embodiments.

In some embodiments of any one of the embodiments described herein, at least one elastic layer is characterized by an elastic modulus (Young's modulus) in a range of from 1 kPa to 300 MPa. In some such embodiments, the elastic modulus is in a range of from 1 kPa to 100 MPa. In some such embodiments, the elastic modulus is in a range of from 1 kPa to 30 MPa. In some such embodiments, the elastic modulus is in a range of from 1 kPa to 10 MPa. In some such embodiments, the elastic modulus is in a range of from 1 kPa to 3 MPa. In some such embodiments, the elastic modulus is in a range of from 1 kPa to 1 MPa. In some such embodiments, the elastic modulus is in a range of from 3 kPa to 1 MPa. In some such embodiments, the elastic modulus is in a range of from 10 kPa to 1 MPa. In some such embodiments, the elastic modulus is in a range of from 30 kPa to 1 MPa. In some such embodiments, each of the elastic layers in a matrix (according to any of the respective embodiments described herein) is characterized by an elastic modulus in a range according to any of the aforementioned embodiments.

In some embodiments of any one of the embodiments described herein, at least one elastic layer is characterized by an elastic modulus (Young's modulus) in a range of from 3 kPa to 1 GPa. In some such embodiments, the elastic modulus is in a range of from 10 kPa to 1 GPa. In some such embodiments, the elastic modulus is in a range of from 30 kPa to 1 GPa. In some such embodiments, the elastic modulus is in a range of from 100 kPa to 1 GPa. In some such embodiments, the elastic modulus is in a range of from 300 kPa to 1 GPa. In some such embodiments, the elastic modulus is in a range of from 300 kPa to 300 MPa. In some such embodiments, the elastic modulus is in a range of from 300 kPa to 100 MPa. In some such embodiments, the elastic modulus is in a range of from 300 kPa to 30 MPa. In some such embodiments, the elastic modulus is in a range of from 300 kPa to 10 MPa. In some such embodiments, each of the elastic layers in a core matrix (according to any of the respective embodiments described herein) is characterized by an elastic modulus in a range according to any of the aforementioned embodiments.

In some embodiments of any one of the embodiments described herein, at least one elastic layer is characterized by an elongation at failure of at least 10%. In some such embodiments, the elongation at failure is in a range of from 10% to 1000%. In some such embodiments, the elongation at failure is at least 20%. In some such embodiments, the elongation at failure is in a range of from 20% to 1000%. In some such embodiments, the elongation at failure is at least 50%. In some such embodiments, the elongation at failure is in a range of from 50% to 1000%. In some such embodiments, the elongation at failure is at least 100%. In some such embodiments, the elongation at failure is in a range of from 100% to 1000%. In some such embodiments, the elongation at failure is at least 200%. In some such embodiments, the elongation at failure is in a range of from 200% to 1000%. In some such embodiments, the elongation at failure is in a range of from 200% to 600%. In some such embodiments, each of the elastic layers in a core matrix (according to any of the respective embodiments described herein) is characterized by an elongation at failure in a range according to any of the aforementioned embodiments.

In some embodiments of any one of the embodiments described herein, at least one elastic layer is characterized by an elongation at failure of at least 10% (according to any of the respective embodiments described herein) and an elastic modulus in a range of from 1 kPa to 1 GPa (according to any of the respective embodiments described herein). In some such embodiments, each of the elastic layers in a matrix (according to any of the respective embodiments described herein) is characterized by an elongation at failure and elastic modulus in a range according to any of the aforementioned embodiments.

In some embodiments of any one of the embodiments described herein, at least one elastic layer is characterized by an elongation at failure of at least 100% (according to any of the respective embodiments described herein) and a recovery of at least 75% (according to any of the respective embodiments described herein). In some such embodiments, each of the elastic layers in a core matrix (according to any of the respective embodiments described herein) is characterized by an elongation at failure and recovery in a range according to any of the aforementioned embodiments.

In some embodiments of any one of the embodiments described herein, at least one elastic layer is characterized by an elastic modulus in a range of from 1 kPa to 1 GPa (according to any of the respective embodiments described herein) and a recovery of at least 75% (according to any of the respective embodiments described herein). In some such embodiments, each of the elastic layers in a matrix (according to any of the respective embodiments described herein) is characterized by an elastic modulus and recovery in a range according to any of the aforementioned embodiments.

In some such embodiments, the elongation at failure is at least 100%. In some such embodiments, the elongation at failure is in a range of from 100% to 1000%. In some such embodiments, the elongation at failure is at least 200%. In some such embodiments, the elongation at failure is in a range of from 200% to 1000%. In some such embodiments, the elongation at failure is in a range of from 200% to 600%. In some such embodiments, each of the elastic layers in a matrix (according to any of the respective embodiments described herein) is characterized by an elongation at failure in a range according to any of the aforementioned embodiments.

In some embodiments of any one of the embodiments described herein, at least one elastic layer is characterized by an ultimate tensile strength of at least 0.05 MPa. In some embodiments of any one of the embodiments described herein, at least one elastic layer is characterized by an ultimate tensile strength of at least 1 MPa. In some embodiments of any one of the embodiments described herein, at least one elastic layer is characterized by an ultimate tensile strength of at least 2 MPa. In some embodiments of any one of the embodiments described herein, at least one elastic layer is characterized by an ultimate tensile strength of at least 4 MPa. In some such embodiments, each of the elastic layers in a matrix (according to any of the respective embodiments described herein) is characterized by an ultimate tensile strength according to any of the aforementioned embodiments.

In some embodiments of any one of the embodiments described herein, at least one elastic layer is characterized by an ultimate tensile strength of at least 0.05 MPa, and an elongation at failure of at least 100%. In some such embodiments, the elongation at failure is in a range of from 100% to 1000%. In some such embodiments, the elongation at failure is at least 200%. In some such embodiments, the elongation at failure is in a range of from 200% to 1000%. In some such embodiments, the elongation at failure is in a range of from 200% to 600%. In some such embodiments, each of the elastic layers in a matrix (according to any of the respective embodiments described herein) is characterized by an ultimate tensile strength and elongation at failure in a range according to any of the aforementioned embodiments.

In some embodiments of any one of the embodiments described herein, at least one elastic layer is characterized by an ultimate tensile strength of at least 1 MPa, and an elongation at failure of at least 100%. In some such embodiments, the elongation at failure is in a range of from 100% to 1000%. In some such embodiments, the elongation at failure is at least 200%. In some such embodiments, the elongation at failure is in a range of from 200% to 1000%. In some such embodiments, the elongation at failure is in a range of from 200% to 600%. In some such embodiments, each of the elastic layers in a core matrix (according to any of the respective embodiments described herein) is characterized by an ultimate tensile strength and elongation at failure in a range according to any of the aforementioned embodiments.

In some embodiments of any one of the embodiments described herein, at least one elastic layer is characterized by an ultimate tensile strength of at least 2 MPa, and an elongation at failure of at least 100%. In some such embodiments, the elongation at failure is in a range of from 100% to 1000%. In some such embodiments, the elongation at failure is at least 200%. In some such embodiments, the elongation at failure is in a range of from 200% to 1000%. In some such embodiments, the elongation at failure is in a range of from 200% to 600%. In some such embodiments, each of the elastic layers in a core matrix (according to any of the respective embodiments described herein) is characterized by an ultimate tensile strength and elongation at failure in a range according to any of the aforementioned embodiments.

In some embodiments of any one of the embodiments described herein, at least one elastic layer is characterized by an ultimate tensile strength of at least 4 MPa, and an elongation at failure of at least 100%. In some such embodiments, the elongation at failure is in a range of from 100% to 1000%. In some such embodiments, the elongation at failure is at least 200%. In some such embodiments, the elongation at failure is in a range of from 200% to 1000%. In some such embodiments, the elongation at failure is in a range of from 200% to 600%. In some such embodiments, each of the elastic layers in a matrix (according to any of the respective embodiments described herein) is characterized by an ultimate tensile strength and elongation at failure in a range according to any of the aforementioned embodiments.

In most embodiments, the mechanical properties of the matrix as a whole will be strongly dependent on the mechanical properties of the elastic layer.

In some embodiments of any one of the embodiments described herein, the matrix (according to any of the respective embodiments described herein) is characterized by an elastic modulus which is within a range of 50% to 200% of an elastic modulus of at least one of the elastic layers, and optionally within a range of 50% to 200% of an elastic modulus of each of the elastic layers in the matrix. In some embodiments, the matrix elastic modulus is within a range of 80% to 120% of an elastic modulus of at least one of the elastic layers. In some embodiments, the matrix elastic modulus is within a range of 80% to 120% of an elastic modulus of each of the elastic layers in the matrix. In some embodiments of any of the aforementioned embodiments, the matrix contains one viscoelastic layer interposed between two elastic layers (according to any of the respective embodiments described herein), and the matrix elastic modulus is within a range of 50% to 200% (and optionally 80% to 120%) of an elastic modulus of at least one (optionally both) of the aforementioned two elastic layers.

The Viscoelastic Layer:

A viscoelastic polymeric material and/or viscoelastic layer according to any one of the embodiments described in this section described in this section may be combined with an elastic layer according to any one of the respective embodiments described herein.

In some embodiments of any one of the embodiments described herein relating to a viscoelastic polymeric material, the viscoelastic polymeric material comprises a polymer characterized by a glass transition temperature and/or melting point at a temperature below 40° C. In some embodiments, the polymer is characterized by a glass transition temperature and/or melting point at a temperature below 35° C. In some embodiments, the polymer is characterized by a glass transition temperature and/or melting point at a temperature below 30° C. In some embodiments, the polymer is characterized by a glass transition temperature and/or melting point at a temperature below 25° C. In some embodiments, the polymer is characterized by a glass transition temperature and/or melting point at a temperature below 20° C. In some embodiments, the polymer is characterized by a glass transition temperature and/or melting point at a temperature below 15° C. In some embodiments, the polymer is characterized by a glass transition temperature and/or melting point at a temperature below 10° C. In some embodiments, the polymer is characterized by a glass transition temperature and/or melting point at a temperature below 5° C. In some embodiments, the polymer is characterized by a glass transition temperature and/or melting point at a temperature below 0° C.

Herein, a glass transition temperature is preferably determined according to differential scanning calorimetry, using procedures accepted in the art for such a purpose, using cooling and heating rates of 10° C. per minute. The glass transition typically appears as an intersection between two linear regions in a plot of heat capacity as a function of temperature.

In some embodiments of any one of the embodiments described herein, the viscoelastic polymeric material comprises a polymer characterized by a glass transition temperature and/or melting point at a temperature which is at least 5° C. lower than an ambient temperature of the composition-of-matter. In some such embodiments, the glass transition temperature and/or melting point is at a temperature which is at least 10° C. lower than an ambient temperature of the composition-of-matter. In some such embodiments, glass transition temperature and/or melting point is at a temperature which is at least 20° C. lower than an ambient temperature of the composition-of-matter.

In some embodiments of any one of the embodiments described herein, the viscoelastic polymeric material comprises a polymer characterized by a glass transition temperature at a temperature which is at least 5° C. lower than an ambient temperature of the composition-of-matter. In some such embodiments, the glass transition temperature is at a temperature which is at least 10° C. lower than an ambient temperature of the composition-of-matter. In some such embodiments, glass transition temperature is at a temperature which is at least 20° C. lower than an ambient temperature of the composition-of-matter.

Herein, the phrase "ambient temperature of the composition-of-matter" generally refers to 20° C., except in the context of articles-of-manufacture comprising the composition-of-matter, in which case the phrase "ambient temperature of the composition-of-matter" refers to a temperature at which the article-of-manufacture is typically used, for example, body temperature in the context of an article-of-manufacture (e.g., medical device) for use inside a body (i.e., 37° C. for articles-of-manufacture for use inside a human body).

Without being bound by any particular theory, it is believed that for a relatively amorphous (i.e., relatively low-crystallinity) polymer, the glass transition temperature has a relatively strong effect on the rheological and mechanical properties of the polymer, whereas a melting point may be less significant and even absent. Similarly, is believed that for a relatively crystalline (i.e., relatively high-crystallinity) polymer, the melting point has a relatively strong effect on the rheological and mechanical properties of the polymer, whereas a glass transition temperature may be less significant and even absent.

In some embodiments of any one of the embodiments described herein relating to a viscoelastic polymeric material, the viscoelastic polymeric material comprises a polymer characterized by a crystallinity of at least 20%, and a melting point at a temperature below 40° C. In some such embodiments, the polymer is characterized by a melting point at a temperature below 35° C. In some such embodiments, the polymer is characterized by a melting point at a temperature below 30° C. In some such embodiments, the polymer is characterized by a melting point at a temperature below 25° C. In some embodiments, the polymer is characterized by a melting point at a temperature below 20° C. In some embodiments, the polymer is characterized by a melting point at a temperature below 15° C. In some embodiments, the polymer is characterized by a melting point at a temperature below 10° C. In some embodiments, the polymer is characterized by a melting point at a temperature below 5° C. In some embodiments, the polymer is characterized by a melting point at a temperature below 0° C.

In some embodiments of any one of the embodiments described herein relating to a viscoelastic polymeric material, the viscoelastic polymeric material comprises a polymer characterized by a crystallinity of at least 30%, and a melting point at a temperature below 40° C. In some such embodiments, the polymer is characterized by a melting point at a temperature below 35° C. In some such embodiments, the polymer is characterized by a melting point at a temperature below 30° C. In some such embodiments, the polymer is characterized by a melting point at a temperature below 25° C. In some embodiments, the polymer is characterized by a melting point at a temperature below 20° C. In some embodiments, the polymer is characterized by a melting point at a temperature below 15° C. In some embodiments, the polymer is characterized by a melting point at a temperature below 10° C. In some embodiments, the polymer is characterized by a melting point at a temperature below 5° C. In some embodiments, the polymer is characterized by a melting point at a temperature below 0° C.

In some embodiments of any one of the embodiments described herein relating to a viscoelastic polymeric material, the viscoelastic polymeric material comprises a polymer characterized by a crystallinity of at least 40%, and a melting point at a temperature below 40° C. In some such embodiments, the polymer is characterized by a melting point at a temperature below 35° C. In some such embodiments, the polymer is characterized by a melting point at a temperature below 30° C. In some such embodiments, the polymer is characterized by a melting point at a temperature below 25° C. In some embodiments, the polymer is characterized by a melting point at a temperature below 20° C. In some embodiments, the polymer is characterized by a melting point at a temperature below 15° C. In some embodiments, the polymer is characterized by a melting point at a temperature below 10° C. In some embodiments, the polymer is characterized by a melting point at a temperature below 5° C. In some embodiments, the polymer is characterized by a melting point at a temperature below 0° C.

In some embodiments of any one of the embodiments described herein relating to a viscoelastic polymeric material, the viscoelastic polymeric material comprises a polymer characterized by a crystallinity of at least 50%, and a melting point at a temperature below 40° C. In some such embodiments, the polymer is characterized by a melting point at a temperature below 35° C. In some such embodiments, the polymer is characterized by a melting point at a temperature below 30° C. In some such embodiments, the polymer is characterized by a melting point at a temperature below 25° C. In some embodiments, the polymer is characterized by a melting point at a temperature below 20° C. In some embodiments, the polymer is characterized by a melting point at a temperature below 15° C. In some embodiments, the polymer is characterized by a melting point at a temperature below 10° C. In some embodiments, the polymer is characterized by a melting point at a temperature below 5° C. In some embodiments, the polymer is characterized by a melting point at a temperature below 0° C.

In some embodiments of any one of the embodiments described herein relating to a viscoelastic polymeric material, the viscoelastic polymeric material comprises a polymer characterized by a crystallinity of at least 60%, and a melting point at a temperature below 40° C. In some such embodiments, the polymer is characterized by a melting point at a temperature below 35° C. In some such embodiments, the polymer is characterized by a melting point at a temperature below 30° C. In some such embodiments, the polymer is characterized by a melting point at a temperature below 25° C. In some embodiments, the polymer is characterized by a melting point at a temperature below 20° C. In some embodiments, the polymer is characterized by a melting point at a temperature below 15° C. In some embodiments, the polymer is characterized by a melting point at a temperature below 10° C. In some embodiments, the polymer is characterized by a melting point at a temperature below 5° C. In some embodiments, the polymer is characterized by a melting point at a temperature below 0° C.

In some embodiments of any one of the embodiments described herein relating to a viscoelastic polymeric material, the viscoelastic polymeric material comprises a polymer characterized by a crystallinity of at least 70%, and a melting point at a temperature below 40° C. In some such embodiments, the polymer is characterized by a melting point at a temperature below 35° C. In some such embodiments, the polymer is characterized by a melting point at a temperature below 30° C. In some such embodiments, the polymer is characterized by a melting point at a temperature below 25° C. In some embodiments, the polymer is characterized by a melting point at a temperature below 20° C. In some embodiments, the polymer is characterized by a melting point at a temperature below 15° C. In some embodiments, the polymer is characterized by a melting point at a temperature below 10° C. In some embodiments, the polymer is characterized by a melting point at a temperature below 5° C. In some embodiments, the polymer is characterized by a melting point at a temperature below 0° C.

In some embodiments of any one of the embodiments described herein relating to a viscoelastic polymeric material, the viscoelastic polymeric material comprises a polymer characterized by a crystallinity of at least 80%, and a melting point at a temperature below 40° C. In some such embodiments, the polymer is characterized by a melting point at a temperature below 35° C. In some such embodiments, the polymer is characterized by a melting point at a temperature below 30° C. In some such embodiments, the polymer is characterized by a melting point at a temperature below 25° C. In some embodiments, the polymer is characterized by a melting point at a temperature below 20° C. In some embodiments, the polymer is characterized by a melting point at a temperature below 15° C. In some embodiments, the polymer is characterized by a melting point at a temperature below 10° C. In some embodiments, the polymer is characterized by a melting point at a temperature below 5° C. In some embodiments, the polymer is characterized by a melting point at a temperature below 0° C.

In some embodiments of any one of the embodiments described herein relating to a viscoelastic polymeric material, the viscoelastic polymeric material comprises a polymer characterized by a crystallinity of less than 80%, and a glass transition temperature at a temperature below 40° C. In some such embodiments, the polymer is characterized by a glass transition temperature at a temperature below 35° C. In some such embodiments, the polymer is characterized by a glass transition temperature at a temperature below 30° C. In some such embodiments, the polymer is characterized by a glass transition temperature at a temperature below 25° C. In some embodiments, the polymer is characterized by a glass transition temperature at a temperature below 20° C. In some embodiments, the polymer is characterized by a glass transition temperature at a temperature below 15° C. In some embodiments, the polymer is characterized by a glass transition temperature at a temperature below 10° C. In some embodiments, the polymer is characterized by a glass transition temperature at a temperature below 5° C. In some embodiments, the polymer is characterized by a glass transition temperature at a temperature below 0° C.

In some embodiments of any one of the embodiments described herein relating to a viscoelastic polymeric material, the viscoelastic polymeric material comprises a polymer characterized by a crystallinity of less than 70%, and a glass transition temperature at a temperature below 40° C. In some such embodiments, the polymer is characterized by a glass transition temperature at a temperature below 35° C. In some such embodiments, the polymer is characterized by a glass transition temperature at a temperature below 30° C. In some such embodiments, the polymer is characterized by a glass transition temperature at a temperature below 25° C. In some embodiments, the polymer is characterized by a glass transition temperature at a temperature below 20° C. In some embodiments, the polymer is characterized by a glass transition temperature at a temperature below 15° C. In some embodiments, the polymer is characterized by a glass transition temperature at a temperature below 10° C. In some embodiments, the polymer is characterized by a glass transition temperature at a temperature below 5° C. In some embodiments, the polymer is characterized by a glass transition temperature at a temperature below 0° C.

In some embodiments of any one of the embodiments described herein relating to a viscoelastic polymeric material, the viscoelastic polymeric material comprises a polymer characterized by a crystallinity of less than 60%, and a glass transition temperature at a temperature below 40° C. In some such embodiments, the polymer is characterized by a glass transition temperature at a temperature below 35° C. In some such embodiments, the polymer is characterized by a glass transition temperature at a temperature below 30° C. In some such embodiments, the polymer is characterized by a glass transition temperature at a temperature below 25° C. In some embodiments, the polymer is characterized by a glass transition temperature at a temperature below 20° C. In some embodiments, the polymer is characterized by a glass transition temperature at a temperature below 15° C. In some embodiments, the polymer is characterized by a glass transition temperature at a temperature below 10° C. In some embodiments, the polymer is characterized by a glass transition temperature at a temperature below 5° C. In some embodiments, the polymer is characterized by a glass transition temperature at a temperature below 0° C.

In some embodiments of any one of the embodiments described herein relating to a viscoelastic polymeric material, the viscoelastic polymeric material comprises a polymer characterized by a crystallinity of less than 50%, and a glass transition temperature at a temperature below 40° C. In some such embodiments, the polymer is characterized by a glass transition temperature at a temperature below 35° C. In some such embodiments, the polymer is characterized by a glass transition temperature at a temperature below 30° C. In some such embodiments, the polymer is characterized by a glass transition temperature at a temperature below 25° C. In some embodiments, the polymer is characterized by a glass transition temperature at a temperature below 20° C. In some embodiments, the polymer is characterized by a glass transition temperature at a temperature below 15° C. In some embodiments, the polymer is characterized by a glass transition temperature at a temperature below 10° C. In some embodiments, the polymer is characterized by a glass transition temperature at a temperature below 5° C. In some embodiments, the polymer is characterized by a glass transition temperature at a temperature below 0° C.

In some embodiments of any one of the embodiments described herein relating to a viscoelastic polymeric material, the viscoelastic polymeric material comprises a polymer characterized by a crystallinity of less than 40%, and a glass transition temperature at a temperature below 40° C. In some such embodiments, the polymer is characterized by a glass transition temperature at a temperature below 35° C. In some such embodiments, the polymer is characterized by a glass transition temperature at a temperature below 30° C. In some such embodiments, the polymer is characterized by a glass transition temperature at a temperature below 25° C. In some embodiments, the polymer is characterized by a glass transition temperature at a temperature below 20° C. In some embodiments, the polymer is characterized by a glass transition temperature at a temperature below 15° C. In some embodiments, the polymer is characterized by a glass transition temperature at a temperature below 10° C. In some embodiments, the polymer is characterized by a glass transition temperature at a temperature below 5° C. In some embodiments, the polymer is characterized by a glass transition temperature at a temperature below 0° C.

In some embodiments of any one of the embodiments described herein relating to a viscoelastic polymeric material, the viscoelastic polymeric material comprises a polymer characterized by a crystallinity of less than 30%, and a glass transition temperature at a temperature below 40° C. In some such embodiments, the polymer is characterized by a glass transition temperature at a temperature below 35° C. In some such embodiments, the polymer is characterized by a glass transition temperature at a temperature below 30° C. In some such embodiments, the polymer is characterized by a glass transition temperature at a temperature below 25° C. In some embodiments, the polymer is characterized by a glass transition temperature at a temperature below 20° C. In some embodiments, the polymer is characterized by a glass transition temperature at a temperature below 15° C. In some embodiments, the polymer is characterized by a glass transition temperature at a temperature below 10° C. In some embodiments, the polymer is characterized by a glass transition temperature at a temperature below 5° C. In some embodiments, the polymer is characterized by a glass transition temperature at a temperature below 0° C.

In some embodiments of any one of the embodiments described herein relating to a viscoelastic polymeric material, the viscoelastic polymeric material comprises a polymer characterized by a crystallinity of less than 20%, and a glass transition temperature at a temperature below 40° C. In some such embodiments, the polymer is characterized by a glass transition temperature at a temperature below 35° C. In some such embodiments, the polymer is characterized by a glass transition temperature at a temperature below 30° C. In some such embodiments, the polymer is characterized by a glass transition temperature at a temperature below 25° C. In some embodiments, the polymer is characterized by a glass transition temperature at a temperature below 20° C. In some embodiments, the polymer is characterized by a glass transition temperature at a temperature below 15° C. In some embodiments, the polymer is characterized by a glass transition temperature at a temperature below 10° C. In some embodiments, the polymer is characterized by a glass transition temperature at a temperature below 5° C. In some embodiments, the polymer is characterized by a glass transition temperature at a temperature below 0° C.

In some embodiments of any one of the embodiments described herein relating to a viscoelastic polymeric material, the viscoelastic polymeric material comprises a polymer characterized by a crystallinity of less than 10%, and a glass transition temperature at a temperature below 40° C. In some such embodiments, the polymer is characterized by a glass transition temperature at a temperature below 35° C. In some such embodiments, the polymer is characterized by a glass transition temperature at a temperature below 30° C. In some such embodiments, the polymer is characterized by a glass transition temperature at a temperature below 25° C. In some embodiments, the polymer is characterized by a glass transition temperature at a temperature below 20° C. In some embodiments, the polymer is characterized by a glass transition temperature at a temperature below 15° C. In some embodiments, the polymer is characterized by a glass transition temperature at a temperature below 10° C. In some embodiments, the polymer is characterized by a glass transition temperature at a temperature below 5° C. In some embodiments, the polymer is characterized by a glass transition temperature at a temperature below 0° C.

In some embodiments of any one of the embodiments described herein, the viscoelastic polymeric material comprises (and optionally consists essentially of) one or more polymers which are biocompatible and/or biodegradable (as defined herein).

Poly(lactic acid-co-ε-caprolactone) (optionally poly(DL-lactic acid-co-ε-caprolactone, either alone or in combination with poly(L-lactic acid-co-ε-caprolactone) and/or poly(D-lactic acid-co-ε-caprolactone)) is an exemplary biocompatible and biodegradable polymer, which may be included in a viscoelastic polymeric material according to any of the respective embodiments described herein. In some such embodiments, the viscoelastic polymeric material consists essentially of poly(lactic acid-co-ε-caprolactone).

In some embodiments of any one of the embodiments described herein, the viscoelastic polymeric material comprises (and optionally consists essentially of) any one or more of the polymers and/or copolymers described herein for use in an elastic layer.

The skilled practitioner will be readily capable of selecting concentrations of polymers, molecular weights of polymers and/or molar ratios of monomers (e.g., lactic acid and ε-caprolactone) in copolymers which may provide elastic or viscoelastic properties according to any of the respective embodiments described herein relating to elastic and/or viscoelastic polymeric materials.

In some embodiments of any one of the embodiments described herein, the viscoelastic polymeric material comprises (and optionally consists essentially of) one or more hydrophobic polymers.

Without being bound by any particular theory, it is believed that a hydrophobic polymer may considerably reduce water-permeability of the matrix, even in embodiments in which the viscoelastic polymeric layer is not in a form of a continuous film. For example, pores in a porous hydrophobic viscoelastic polymeric layer may be too small to allow passage of water, as contact between the water and hydrophobic polymer is energetically unfavorable.

Herein, a "hydrophobic polymer" is a polymer characterized in that in water at a pH of 7.0, the polymer (in bulk) has a solubility of less than 1 gram per liter, and does not absorb more than 20 weight percents of water (weight of absorbed water relative to weight of polymer). In some embodiments, the hydrophobic polymer is characterized in that it does not absorb more than 10 weight percents of water at pH 7.0. In some embodiments, the hydrophobic polymeric substance is characterized in that it does not absorb more than 5 weight percents of water at pH 7.0. In some embodiments, the hydrophobic polymeric substance is characterized in that it does not absorb more than 2 weight percents of water at pH 7.0. In some embodiments, the hydrophobic polymeric substance is characterized in that it does not absorb more than 1 weight percents of water at pH 7.0.

The skilled practitioner will be readily capable of selecting polymers (e.g., polymers described herein), molecular weights of polymers and/or molar ratios of monomers (e.g., lactic acid and ε-caprolactone) in copolymers which result in a hydrophobic polymer as defined herein.

In some embodiments of any one of the embodiments described herein, a viscoelastic layer (according to any one of the respective embodiments described herein) is characterized by a mean thickness in a range of from 1 to 300 μm. In some such embodiments, the mean thickness is in a range of from 2 to 250 μm. In some such embodiments, the mean thickness is in a range of from 3 to 200 µm. In some such embodiments, the mean thickness is in a range of from 5 to 150 µm. In some such embodiments, the mean thickness is in a range of from 10 to 100 µm. In some such embodiments, the mean thickness is in a range of from 15 to 60 µm.

In some embodiments of any one of the embodiments described herein, a viscoelastic layer (according to any one of the respective embodiments described herein) is characterized by a mean thickness in a range of from 1 to 200 µm. In some such embodiments, the mean thickness is in a range of from 1 to 100 µm. In some such embodiments, the mean thickness is in a range of from 1 to 60 µm. In some such embodiments, the mean thickness is in a range of from 1 to 30 µm.

In some embodiments of any one of the embodiments described herein, a viscoelastic layer (according to any one of the respective embodiments described herein) is characterized by a mean thickness in a range of from 2 to 300 µm. In some such embodiments, the mean thickness is in a range of from 5 to 300 µm. In some such embodiments, the mean thickness is in a range of from 10 to 300 µm. In some such embodiments, the mean thickness is in a range of from 20 to 300 µm. In some such embodiments, the mean thickness is in a range of from 40 to 300 µm. In some embodiments of any one of the embodiments described herein, a viscoelastic layer (according to any of the respective embodiments described herein) is a non-porous, continuous film or is characterized by a limited porosity.

In some embodiments of any one of the embodiments described herein, a viscoelastic layer is characterized by a porosity which is lower than a porosity of each of the adjacent elastic layers (according to any of the respective embodiments described herein). In some such embodiments, the viscoelastic layer is characterized by a porosity which is less than 75% of a porosity of each of the adjacent elastic layers (according to any of the respective embodiments described herein). In some such embodiments, the viscoelastic layer is characterized by a porosity which is less than 50% of a porosity of each of the adjacent elastic layers (according to any of the respective embodiments described herein). In some such embodiments, the viscoelastic layer is characterized by a porosity which is less than 25% of a porosity of each of the adjacent elastic layers (according to any of the respective embodiments described herein). In some such embodiments, the viscoelastic layer is characterized by a porosity which is less than 15% of a porosity of each of the adjacent elastic layers (according to any of the respective embodiments described herein). In some such embodiments, the viscoelastic layer is characterized by a porosity which is less than 10% of a porosity of each of the adjacent elastic layers (according to any of the respective embodiments described herein). In some such embodiments, the viscoelastic layer is characterized by a porosity which is less than 5% of a porosity of each of the adjacent elastic layers (according to any of the respective embodiments described herein). In some embodiments of any one of the aforementioned embodiments relating to porosity of the viscoelastic layer(s), the elastic layers are characterized by a porosity of at least 50% (e.g., from 50 to 99%), according to any of the respective embodiments described herein.

In some embodiments of any one of the embodiments described herein, a viscoelastic layer is characterized by a porosity in a range of from 0 to 50%. In some such embodiments, the porosity is from 0 to 40%. In some such embodiments, the porosity is from 0 to 30%. In some such embodiments, the porosity is from 0 to 20%. In some such embodiments, the porosity is from 0 to 10%. In some such embodiments, a porosity of each of the adjacent elastic layers is higher than the porosity of the viscoelastic layer (e.g., more than 50%).

Without being bound by any particular theory, it is believed that a viscoelastic layer which is non-porous or characterized by limited porosity (e.g., up to 50%) reduces a permeability of the core matrix to water as well as other liquids, thereby enhancing the ability of the composition-of-matter to serve, for example, as a sealant against fluid leakage. It is further believed that such a layer, for example, a layer which does not have any fibrous structure, can readily undergo deformation in response to stress by viscous flow, and that such deformation can result in closure of holes formed in the viscoelastic layer.

In some embodiments of any one of the embodiments described herein, the viscoelastic layer is characterized by a porosity (e.g., up to 50%) which is lower than a porosity of the elastic layers (according to any of the respective embodiments described herein, optionally embodiments wherein a porosity of the elastic layers is at least 50%, at least 60%, at least 70%, at least 80% and/or at least 90%). In some such embodiments, the viscoelastic layer porosity is no more than half of the elastic layer porosity.

Without being bound by any particular theory, it is believed that the viscoelastic layer acts as a barrier (e.g., to water-permeation), which may be more impermeable than elastic layers which are more porous than the viscoelastic layer (e.g., porous elastic layers made of fibers), thereby significantly reducing permeability of matrices comprising such elastic layers.

A continuous film may optionally be prepared, for example, by film casting (e.g., as exemplified herein).

A limited porosity may optionally be prepared, for example, by forming fibers of the viscoelastic polymeric material, for example, by electrospinning (e.g., as exemplified herein), wherein the fibers partially merge as a result of viscous flow (which is optionally enhanced by heat treatment and/or pressure), thereby resulting in smaller pores and lower porosity.

In some embodiments of any one of the embodiments described herein, the viscoelastic layer has a fibrous structure. In some such embodiments, the layer comprises fibers which provide mechanical strength, as well as viscoelastic polymeric material in the spaces interposed between the fibers. In some such embodiments, the fibers are more elastic and less fluid than the viscoelastic polymeric material in the spaces interposed between the fibers. For example, in some embodiments, a relatively fluid fraction of the viscoelastic polymeric material exits the fibers by viscous flow, whereas the fraction of the viscoelastic polymeric material remaining in the fibers is more solid and/or elastic in nature.

In some embodiments of any one of the embodiments described herein, a viscoelastic layer (according to any of the respective embodiments described herein) is characterized by at least one of the following 4 properties a) a shear storage modulus (G') in a range of from 0.01 to 10 MPa, at a temperature of 10° C. and frequency of 0.1 Hz;

b) a shear loss modulus (G") in a range of from 0.0001 to 2 MPa, at a temperature of 10° C. and frequency of 0.1 Hz;

c) a glass transition temperature and/or melting point of the viscoelastic polymeric material which is at a temperature below 40° C.; and d) a loss tangent (G"/G') at a temperature of 10° C. and frequency of 0.1 Hz which is in a range of from 0.01 to 4.

In some embodiments of any one of the embodiments described herein, a viscoelastic layer (according to any of the respective embodiments described herein) is characterized by at least two of the abovementioned 4 properties.

In some embodiments of any one of the embodiments described herein, a viscoelastic layer (according to any of the respective embodiments described herein) is characterized by at least 3 of the abovementioned 4 properties.

In some embodiments of any one of the embodiments described herein, a viscoelastic layer (according to any of the respective embodiments described herein) is characterized by each of the abovementioned 4 properties.

In some embodiments of any one of the embodiments described herein, a viscoelastic layer (according to any of the respective embodiments described herein) is characterized by a shear storage modulus (G') in a range of from 0.01 to 10 MPa, at a temperature of 10° C. and frequency of 0.1 Hz. In some such embodiments, the shear storage modulus is in a range of from 0.05 to 10 MPa. In some such embodiments, the shear storage modulus is in a range of from 0.1 to 5 MPa. In some such embodiments, the shear storage modulus is in a range of from 0.2 to 2.5 MPa.

In some embodiments of any one of the embodiments described herein, a viscoelastic layer (according to any of the respective embodiments described herein) is characterized by a shear storage modulus (G') in a range of from 0.01 to 1 MPa, at a temperature of 10° C. and frequency of 0.1 Hz. In some such embodiments, the shear storage modulus is in a range of from 0.05 to 1 MPa. In some such embodiments, the shear storage modulus is in a range of from 0.1 to 1 MPa. In some such embodiments, the shear storage modulus is in a range of from 0.2 to 1 MPa.

In some embodiments of any one of the embodiments described herein, a viscoelastic layer (according to any of the respective embodiments described herein) is characterized by a shear storage modulus (G') in a range of from 0.5 to 10 MPa, at a temperature of 10° C. and frequency of 0.1 Hz. In some such embodiments, the shear storage modulus is in a range of from 1 to 10 MPa. In some such embodiments, the shear storage modulus is in a range of from 2 to 10 MPa.

In some embodiments of any one of the embodiments described herein, a viscoelastic layer (according to any of the respective embodiments described herein) is characterized by a shear loss modulus (G") in a range of from 0.0001 to 2 MPa, at a temperature of 10° C. and frequency of 0.1 Hz. In some such embodiments, the shear loss modulus is in a range of from 0.0003 to 0.3 MPa. In some such embodiments, the shear loss modulus is in a range of from 0.001 to 0.1 MPa. In some such embodiments, the shear loss modulus is in a range of from 0.003 to 0.03 MPa.

In some embodiments of any one of the embodiments described herein, a viscoelastic layer (according to any of the respective embodiments described herein) is characterized by a shear loss modulus (G") in a range of from 0.0001 to 0.3 MPa, at a temperature of 10° C. and frequency of 0.1 Hz. In some such embodiments, the shear loss modulus is in a range of from 0.0001 to 0.1 MPa. In some such embodiments, the shear loss modulus is in a range of from 0.0001 to 0.03 MPa. In some such embodiments, the shear loss modulus is in a range of from 0.0001 to 0.01 MPa. In some such embodiments, the shear loss modulus is in a range of from 0.0001 to 0.003 MPa. In some such embodiments, the shear loss modulus is in a range of from 0.0001 to 0.001 MPa.

In some embodiments of any one of the embodiments described herein, a viscoelastic layer (according to any of the respective embodiments described herein) is characterized by a shear loss modulus (G") in a range of from 0.0003 to 2 MPa, at a temperature of 10° C. and frequency of 0.1 Hz. In some such embodiments, the shear loss modulus is in a range of from 0.001 to 1 MPa. In some such embodiments, the shear loss modulus is in a range of from 0.003 to 1 MPa. In some such embodiments, the shear loss modulus is in a range of from 0.01 to 1 MPa. In some such embodiments, the shear loss modulus is in a range of from 0.03 to 1 MPa. In some such embodiments, the shear loss modulus is in a range of from 0.1 to 1 MPa.

In some embodiments of any one of the embodiments described herein, a viscoelastic layer (according to any of the respective embodiments described herein) is characterized by a loss tangent (G"/G', e.g., wherein values of G" and G' are each individually in accordance with any of the respective embodiments described herein) in a range of from 0.01 to 1, at a temperature of 10° C. and frequency of 0.1 Hz. In some such embodiments, the loss tangent is in a range of from 0.02 to 0.8. In some such embodiments, the loss tangent is in a range of from 0.05 to 0.7. In some such embodiments, the loss tangent is in a range of from 0.1 to 0.6. In some such embodiments, the loss tangent is in a range of from 0.175 to 0.5.

In some embodiments of any one of the embodiments described herein, a viscoelastic layer (according to any of the respective embodiments described herein) is characterized by a loss tangent (G"/G', e.g., wherein values of G" and G' are each individually in accordance with any of the respective embodiments described herein) in a range of from 0.01 to 0.5, at a temperature of 10° C. and frequency of 0.1 Hz. In some such embodiments, the loss tangent is in a range of from 0.01 to 0.3. In some such embodiments, the loss tangent is in a range of from 0.01 to 0.2. In some such embodiments, the loss tangent is in a range of from 0.01 to 0.1.

In some embodiments of any one of the embodiments described herein, a viscoelastic layer (according to any of the respective embodiments described herein) is characterized by a loss tangent (G"/G', e.g., wherein values of G" and G' are each individually in accordance with any of the respective embodiments described herein) in a range of from 0.02 to 1, at a temperature of 10° C. and frequency of 0.1 Hz. In some such embodiments, the loss tangent is in a range of from 0.05 to 1. In some such embodiments, the loss tangent is in a range of from 0.1 to 1. In some such embodiments, the loss tangent is in a range of from 0.2 to 1. In some such embodiments, the loss tangent is in a range of from 0.3 to 1. In some such embodiments, the loss tangent is in a range of from 0.5 to 1.

In some embodiments of any one of the embodiments described herein, a viscoelastic layer (according to any of the respective embodiments described herein) is characterized by a loss tangent (G"/G') in a range of from 0.01 to 1 (according to any of the respective embodiments described herein), and a shear storage modulus (G') in a range of from 0.01 to 10 MPa (according to any of the respective embodiments described herein), at a temperature of 10° C. and frequency of 0.1 Hz. In some such embodiments, the shear storage modulus is in a range of from 0.05 to 10 MPa. In some such embodiments, the shear storage modulus is in a range of from 0.1 to 5 MPa. In some such embodiments, the shear storage modulus is in a range of from 0.2 to 2.5 MPa.

In some embodiments of any one of the embodiments described herein, a viscoelastic layer (according to any of the respective embodiments described herein) is characterized by a loss tangent (G"/G') in a range of from 0.05 to 0.7 (according to any of the respective embodiments described herein), and a shear storage modulus (G') in a range of from 0.01 to 10 MPa (according to any of the respective embodiments described herein), at a temperature of 10° C. and frequency of 0.1 Hz. In some such embodiments, the shear storage modulus is in a range of from 0.05 to 10 MPa. In some such embodiments, the shear storage modulus is in a range of from 0.1 to 5 MPa. In some such embodiments, the shear storage modulus is in a range of from 0.2 to 2.5 MPa.

In some embodiments of any one of the embodiments described herein, a viscoelastic layer (according to any of the respective embodiments described herein) is characterized by a loss tangent (G"/G') in a range of from 0.175 to 0.5 (according to any of the respective embodiments described herein), and a shear storage modulus (G') in a range of from 0.01 to 10 MPa (according to any of the respective embodiments described herein), at a temperature of 10° C. and frequency of 0.1 Hz. In some such embodiments, the shear storage modulus is in a range of from 0.05 to 10 MPa. In some such embodiments, the shear storage modulus is in a range of from 0.1 to 5 MPa. In some such embodiments, the shear storage modulus is in a range of from 0.2 to 2.5 MPa.

In some embodiments of any one of the embodiments described herein, a viscoelastic layer (according to any of the respective embodiments described herein) is characterized by a loss tangent (G"/G') in a range of from 0.01 to 1 (according to any of the respective embodiments described herein), and a shear loss modulus (G") in a range of from 0.0001 to 2 MPa (according to any of the respective embodiments described herein), at a temperature of 10° C. and frequency of 0.1 Hz. In some such embodiments, the shear loss modulus is in a range of from 0.0003 to 0.3 MPa. In some such embodiments, the shear loss modulus is in a range of from 0.001 to 0.1 MPa. In some such embodiments, the shear loss modulus is in a range of from 0.003 to 0.03 MPa.

In some embodiments of any one of the embodiments described herein, a viscoelastic layer (according to any of the respective embodiments described herein) is characterized by a loss tangent (G"/G') in a range of from 0.05 to 0.7 (according to any of the respective embodiments described herein), and a shear loss modulus (G") in a range of from 0.0001 to 2 MPa (according to any of the respective embodiments described herein), at a temperature of 10° C. and frequency of 0.1 Hz. In some such embodiments, the shear loss modulus is in a range of from 0.0003 to 0.3 MPa. In some such embodiments, the shear loss modulus is in a range of from 0.001 to 0.1 MPa. In some such embodiments, the shear loss modulus is in a range of from 0.003 to 0.03 MPa.

In some embodiments of any one of the embodiments described herein, a viscoelastic layer (according to any of the respective embodiments described herein) is characterized by a loss tangent (G"/G') in a range of from 0.175 to 0.5 (according to any of the respective embodiments described herein), and a shear loss modulus (G") in a range of from 0.0001 to 2 MPa (according to any of the respective embodiments described herein), at a temperature of 10° C. and frequency of 0.1 Hz. In some such embodiments, the shear loss modulus is in a range of from 0.0003 to 0.3 MPa. In some such embodiments, the shear loss modulus is in a range of from 0.001 to 0.1 MPa. In some such embodiments, the shear loss modulus is in a range of from 0.003 to 0.03 MPa.

In some embodiments of any one of the embodiments described herein, a viscoelastic layer (according to any of the respective embodiments described herein) is characterized by a shear storage modulus (G') in a range of from 0.01 to 10 MPa (according to any of the respective embodiments described herein), and a shear loss modulus (G") in a range of from 0.0001 to 2 MPa (according to any of the respective embodiments described herein), at a temperature of 10° C. and frequency of 0.1 Hz. In some such embodiments, the shear loss modulus is in a range of from 0.0003 to 0.3 MPa. In some such embodiments, the shear loss modulus is in a range of from 0.001 to 0.1 MPa. In some such embodiments, the shear loss modulus is in a range of from 0.003 to 0.03 MPa.

In some embodiments of any one of the embodiments described herein, a viscoelastic layer (according to any of the respective embodiments described herein) is characterized by a shear storage modulus (G') in a range of from 0.05 to 10 MPa (according to any of the respective embodiments described herein), and a shear loss modulus (G") in a range of from 0.0001 to 2 MPa (according to any of the respective embodiments described herein), at a temperature of 10° C. and frequency of 0.1 Hz. In some such embodiments, the shear loss modulus is in a range of from 0.0003 to 0.3 MPa. In some such embodiments, the shear loss modulus is in a range of from 0.001 to 0.1 MPa. In some such embodiments, the shear loss modulus is in a range of from 0.003 to 0.03 MPa.

In some embodiments of any one of the embodiments described herein, a viscoelastic layer (according to any of the respective embodiments described herein) is characterized by a shear storage modulus (G') in a range of from 0.1 to 5 MPa (according to any of the respective embodiments described herein), and a shear loss modulus (G") in a range of from 0.0001 to 2 MPa (according to any of the respective embodiments described herein), at a temperature of 10° C. and frequency of 0.1 Hz. In some such embodiments, the shear loss modulus is in a range of from 0.0003 to 0.3 MPa. In some such embodiments, the shear loss modulus is in a range of from 0.001 to 0.1 MPa. In some such embodiments, the shear loss modulus is in a range of from 0.003 to 0.03 MPa.

In some embodiments of any one of the embodiments described herein, a viscoelastic layer (according to any of the respective embodiments described herein) is characterized by a shear storage modulus (G') in a range of from 0.2 to 2.5 MPa (according to any of the respective embodiments described herein), and a shear loss modulus (G") in a range of from 0.0001 to 2 MPa (according to any of the respective embodiments described herein), at a temperature of 10° C. and frequency of 0.1 Hz. In some such embodiments, the shear loss modulus is in a range of from 0.0003 to 0.3 MPa. In some such embodiments, the shear loss modulus is in a range of from 0.001 to 0.1 MPa. In some such embodiments, the shear loss modulus is in a range of from 0.003 to 0.03 MPa.

In some embodiments of any one of the embodiments described herein, a viscoelastic layer (according to any of the respective embodiments described herein) is characterized by a loss tangent (G"/G') which is at least 200% of (two-fold) a loss tangent of the elastic layers (according to any of the respective embodiments described herein), at a frequency of 0.1 Hz, and at any temperature within the range of from 0 to 40° C. In some such embodiments, the temperature is 37° C. In some such embodiments, the temperature is 25° C. In some such embodiments, the temperature is 20° C. In some such embodiments, the temperature is 0° C.

In some embodiments of any one of the embodiments described herein, a viscoelastic layer (according to any of the respective embodiments described herein) is characterized by a loss tangent (G"/G') which is at least 300% of (3-fold) a loss tangent of the elastic layers (according to any of the respective embodiments described herein), at a frequency of 0.1 Hz, and at any temperature within the range of from 0 to 40° C. In some such embodiments, the temperature is 37° C. In some such embodiments, the temperature is 25° C. In some such embodiments, the temperature is 20° C. In some such embodiments, the temperature is 0° C.

In some embodiments of any one of the embodiments described herein, a viscoelastic layer (according to any of the respective embodiments described herein) is characterized by a loss tangent (G"/G') which is at least 500% of (5-fold) a loss tangent of the elastic layers (according to any of the respective embodiments described herein), at a frequency of 0.1 Hz, and at any temperature within the range of from 0 to 40° C. In some such embodiments, the temperature is 37° C. In some such embodiments, the temperature is 25° C. In some such embodiments, the temperature is 20° C. In some such embodiments, the temperature is 0° C.

In some embodiments of any one of the embodiments described herein, a viscoelastic layer (according to any of the respective embodiments described herein) is characterized by a loss tangent (G"/G') which is at least 1,000% of (10-fold) a tangent of the elastic layers (according to any of the respective embodiments described herein), at a frequency of 0.1 Hz, and at any temperature within the range of from 0 to 40° C. In some such embodiments, the temperature is 37° C. In some such embodiments, the temperature is 25° C. In some such embodiments, the temperature is 20° C. In some such embodiments, the temperature is 0° C.

In some embodiments of any one of the embodiments described herein, a viscoelastic layer (according to any of the respective embodiments described herein) is characterized by a loss tangent (G"/G') which is at least 3,000% of (30-fold) a loss tangent of the elastic layers (according to any of the respective embodiments described herein), at a frequency of 0.1 Hz, and at any temperature within the range of from 0 to 40° C. In some such embodiments, the temperature is 37° C. In some such embodiments, the temperature is 25° C. In some such embodiments, the temperature is 20° C. In some such embodiments, the temperature is 0° C.

In some embodiments of any one of the embodiments described herein, a viscoelastic layer (according to any of the respective embodiments described herein) is characterized by a loss tangent (G"/G') which is at least 10,000% of (100-fold) a loss tangent of the elastic layers (according to any of the respective embodiments described herein), at a frequency of 0.1 Hz, and at any temperature within the range of from 0 to 40° C. In some such embodiments, the temperature is 37° C. In some such embodiments, the temperature is 25° C. In some such embodiments, the temperature is 20° C. In some such embodiments, the temperature is 0° C.

Without being bound by any particular theory, it is believed that a core matrix wherein the viscoelastic layer has a considerably higher loss tangent (and accordingly, a less solid behavior) than the elastic layers may undergo an elastic deformation in which the viscoelastic polymeric material may concomitantly undergo non-elastic deformation and viscous flow within the core matrix, while the matrix retains elastic properties due to the elastic properties of the elastic layers.

Preparation:

Any of the fibers described herein (according to any one of the respective embodiments) may optionally be produced by any suitable technique for preparing fibers (including macro-sized fibers, micro-sized fibers and nano-sized fibers), such as conventional fiber-spinning techniques. Such techniques include, for example, solution spinning, electrospinning, wet spinning, dry spinning, melt spinning and gel spinning. Each spinning method imparts specific physical dimensions and mechanical properties of the resulting fibers, and can be tuned to give the desired characteristics according to the required application of the fibers and layer of fibers described herein.

Briefly, a fiber spinning technique optionally involves the use of spinnerets. These are similar, in principle, to a bathroom shower head, and may have from one to several hundred small holes. As the filaments, or crude fibers, emerge from the holes in the spinneret, the dissolved or liquefied polymer is converted first to a rubbery state and then solidified. This process of extrusion and solidification of "endless" crude fibers is called spinning, not to be confused with the textile operation of the same name, where short pieces of staple fiber are twisted into yarn.

Wet spinning is used for fiber-forming substances that have been dissolved in a solvent. The spinnerets are submerged in a chemical bath and as the filaments emerge they precipitate from solution and solidify. Because the solution is extruded directly into the precipitating liquid, this process for making fibers is called wet spinning. Fibers such as, for example, acrylic, rayon, aramid, modacrylic and spandex can be produced by this process.

Dry spinning is also used for fiber-forming substances in solution, however, instead of precipitating the polymer by dilution or chemical reaction, solidification is achieved by evaporating the solvent in a stream of air or inert gas. The filaments do not come in contact with a precipitating liquid, eliminating the need for drying and easing solvent recovery. This process may be used for the production of, for example, acetate, triacetate, acrylic, modacrylic, PBI, spandex and vinyon.

In melt spinning, the fiber-forming substance is melted for extrusion through the spinneret and then the crude fibers directly solidified by cooling. Melt spun crude fibers can be extruded from the spinneret in different cross-sectional shapes (round, trilobal, pentagonal, octagonal and others). Nylon (polyamide), olefin, polyester, saran and sulfar, for example, are produced in this manner. Non-polymeric fibers can also be produced by melt-spinning.

Gel spinning is a special process used to obtain high strength or other special fiber properties. The polymer is not in a true liquid state during extrusion. Not completely separated, as they would be in a true solution, the polymer chains are bound together at various points in liquid crystal form. This produces strong inter-chain forces in the resulting filaments that can significantly increase the tensile strength of the fibers. In addition, the liquid crystals are aligned along the fiber axis by the shear forces during extrusion. The filaments emerge with an unusually high degree of orientation relative to each other which increases their strength. The process can also be described as dry-wet spinning, since the filaments first pass through air and then are cooled further in a liquid bath. Some high-strength polyethylene and aramid fibers, for example, are produced by gel spinning.

Alternatively, the fibers can be of natural or synthetic origins, and can be provided ready for use without further manipulation or preparation procedures or upon surface treatment thereof.

In some embodiments of any one of the embodiments described herein, the fibers are formed of electrospun polymeric material.

As used herein, the terms "electrospin", "electrospinning", "electrospun" and the like refer to a technology which produces fibers (e.g., nanofibers) from a polymer solution. During this process, one or more polymers of the polymeric material as described herein are liquefied (i.e., melted or dissolved) and placed in a dispenser. An electrostatic field is employed to generate a positively charged jet from the dispenser to the collector. Thus, a dispenser (e.g., a syringe with metallic needle) is typically connected to a source of high voltage, preferably of positive polarity, while the collector is grounded, thus forming an electrostatic field between the dispenser and the collector. Alternatively, the dispenser can be grounded while the collector is connected to a source of high voltage, preferably with negative polarity. As will be appreciated by one ordinarily skilled in the art, any of the above configurations establishes motion of positively charged jet from the dispenser to the collector. Reverse polarity for establishing motions of a negatively charged jet from the dispenser to the collector is also contemplated. At the critical voltage, the charge repulsion begins to overcome the surface tension of the liquid drop. The charged jets depart from the dispenser and travel within the electrostatic field towards the collector. Moving with high velocity in the inter-electrode space, the jet stretches and the solvent therein evaporates, thus forming fibers which are collected on the collector, e.g., in a form of a layer of fibers.

Several parameters may affect the diameter of the fiber, these include, the size of the dispensing hole of the dispenser, the dispensing rate, the strength of the electrostatic field, the distance between the dispenser and/or the concentration of the polymeric material used for fabricating the electrospun fiber.

The dispenser can be, for example, a syringe with a metal needle or a bath provided with one or more capillary apertures from which the liquefied polymeric material as described herein can be extruded, e.g., under the action of hydrostatic pressure, mechanical pressure, air pressure and high voltage.

According to one embodiment, the collector is a rotating collector which serves for collecting the electrospun fibers thereupon. Employing a rotating collector can result in a layer of electrospun fibers with a continuous gradient of porosity. Such a porosity gradient can be achieved by continuous variation in the velocity of the collector or by a longitudinal motion of the dispenser, these result in a substantial variation in the density and/or spatial distribution of the fibers on the collector and thus, result in a porosity gradient along the radial direction or along the longitudinal direction of the collector, respectively. Typically, but not obligatorily, the rotating collector has a cylindrical shape (e.g., a drum); however, it will be appreciated that the rotating collector can be also of a planar geometry.

According to another embodiment, the collector is a flat ground collector which serves for collecting the electrospun scaffold thereupon. Employing a flat ground collector enables collection of random nanofibers. It will be appreciated that the flat ground collector is typically a horizontal collector or a vertical collector.

In some embodiments of any one of the embodiments described herein, any two or more adjacent layers formed of fibers (including elastic layers and/or viscoelastic layers according to any of the respective embodiments described herein) are optionally prepared by continuous electrospinning.

It is to be appreciated that a viscoelastic layer formed of fibers does not necessarily retain a fibrous structure. For example, as exemplified herein, a viscoelastic layer in a form of a continuous film may be formed from fibers which then merge, thereby losing some or all of the porous and fibrous nature of the layer.

According to an aspect of some embodiments of the invention, there is provided a process of preparing a composition-of-matter and/or core matrix according to any of the respective embodiments described herein, the process comprising forming the one or more elastic layers (e.g., made of polymeric fibers, according to any of the respective embodiments described herein) and the viscoelastic layer(s) by continuous electrospinning, thereby forming the composition-of-matter and/or core matrix.

According to an aspect of some embodiments of the invention, there is provided a process of preparing a composition-of-matter and/or core matrix according to any of the respective embodiments described herein, the process providing the one or more elastic layers and the viscoelastic layer(s) (according to any of the respective embodiments described herein), placing the viscoelastic layer(s) parallel to the elastic layers (optionally between the elastic layers), e.g., in a stacked formation, and pressing the elastic layers and the viscoelastic layer(s) together, thereby forming the composition-of-matter and/or core matrix. In some such embodiments, the process further comprises forming the elastic layers by electrospinning.

In some embodiments, pressing the elastic layers and viscoelastic layer(s) together comprises applying a pressure of at least 1 gram/cm$^2$. In some embodiments, the pressure is at least 2 gram/cm$^2$. In some embodiments, the pressure is at least 4 gram/cm$^2$. In some embodiments, the pressure is at least 8 gram/cm$^2$.

In some embodiments, the process further comprises heating the viscoelastic layer prior to, concomitantly with, and/or subsequently to pressing the layers. In some such embodiments, the heating is to a temperature which is above a glass transition temperature and/or melting point (optionally a glass transition temperature) of a polymer in the viscoelastic layer, in accordance with any of the respective embodiments described herein (e.g., 40° C.).

Optional Applications:

According to another aspect of embodiments of the invention there is provided an article-of-manufacture comprising a composition-of-matter and/or matrix according to any of the respective embodiments described herein.

In some such embodiments, the article-of-manufacture consists essentially of the composition-of-matter, as described herein.

In some such embodiments, the article-of-manufacture comprises additional components in addition the composition-of-matter, as described herein.

Examples of articles-of-manufacture in which a flexible composition-of-matter according to any of the respective embodiments described herein may be advantageously incorporated include, without limitation, articles intended to be applied to surfaces of various shapes, such as packaging materials, coatings, adhesive tape, sealants; articles comprising an inflatable component, such as a balloon (e.g., balloon catheters); and devices with movable parts (wherein the composition-of-matter may optionally be attached to two or more separately movable parts), such as household and/or industrial machinery.

In some embodiments of any one of the embodiments described herein, the article-of-manufacture is a medical device. In some such embodiments, the medical device is an implantable medical device.

In some embodiments of any one of embodiments described herein relating to a medical device, the medical device is for use in the field of general surgery, neurology, ear-nose and throat, urology, gynecology/obstetrics, thoracic, dental/maxillofacial, gastroenterology, plastic surgery, ophthalmology, cardiovascular and/or orthopedic medicine.

In some embodiments of any one of the embodiments described herein, the article-of-manufacture (e.g., medical device) is identified for use in a treatment. In some embodiments, the article-of-manufacture (e.g., medical device) is identified for use in repairing and/or substituting a biological tissue.

According to another aspect of embodiments of the invention, there is provided a method of repairing and/or substituting a biological tissue in a subject in need thereof, the method comprising contacting the biological tissue with article-of-manufacture (e.g., medical device) described herein.

In some embodiments of any of the embodiments described herein relating to repairing and/or substituting a biological tissue, a biological tissue to be repaired and/or substituted is a membrane (e.g., following traumatic injury, hernia and/or surgical incision of the membrane). In some embodiments, the membrane to be repaired and/or substituted is dura mater (e.g., following traumatic injury and/or surgical incision of the dura mater). In some embodiments, the article-of-manufacture has a sheet-like geometry (e.g., as described herein) which mimics that of a membrane.

Examples of treatments for which an article-of-manufacture according to such embodiments may be used (e.g., by implantation and/or temporary internal or topical use) in a treatment or method described herein (according to any of the respective embodiments) include, without limitation, repairing and/or substituting a biological tissue, such as dural repair, hernia repair, internal and/or topical wound closure, skin closure and/or repair (e.g., as part of plastic surgery), supporting another medical implant (such as in breast reconstruction surgery), sealing tissues and/or organs in order to contain bodily fluids and/or air (e.g., treating bile duct leakage), sealing an anastomosis, inhibition of post-surgical adhesions between tissues and promotion of hemostasis (e.g., wherein the matrix is coated with thrombin and/or fibrinogen and/or fibrin); as well as administration of a therapeutically effective agent (e.g., by incorporating the therapeutically effective agent in and/or on the core matrix, according to any of the embodiments described herein relating to inclusion of an additional ingredient).

Examples of treatments for which an implantable medical device according to embodiments described herein may be identified for use include, without limitation, dural repair, hernia repair, internal wound closure, sealing tissues and/or organs in order to contain bodily fluids and/or air, sealing an anastomosis, inhibition of post-surgical adhesions between tissues, promotion of hemostasis, and administration of a therapeutically effective agent.

In some embodiments of any of the embodiments described herein, the medical device is configured for eluting a therapeutically active agent, e.g., an agent included as an additional ingredient according to any of the respective embodiments described herein. In some such embodiments, the medical device is a stent. Optionally, the composition-of-matter forms at least a portion of a flexible sleeve of the stent.

The therapeutically active agent may optionally be incorporated within a core matrix and/or on a surface of the core matrix. Optionally, the therapeutically active agent is incorporated within a drug-eluting layer within the core matrix and/or on a surface of the core matrix. Such a drug eluting layer may be formed of any suitable substance known in the art of drug-eluting layers.

Herein, the phrase "repairing and/or substituting a biological tissue" refers to repair of tissue which is physically damaged in any manner, and encompasses supporting and/or holding damaged tissue together in vivo or ex vivo, as well as filling gaps formed by an absence of tissue (substituting tissue). The damaged tissue may be damaged, for example, by detachment (e.g., tearing, cutting), compressive stress, tensile stress, shear stress, cellular dysfunction and/or cell death.

In some embodiments of any of the embodiments described herein relating to repairing and/or substituting a biological tissue, the repairing and/or substituting a biological tissue comprises suturing the article-of-manufacture to the tissue (that is, the article-of-manufacture and tissue are attached via at least one suture).

As exemplified herein, core matrices described herein are particularly suitable for being sutured without losing mechanical or functional integrity.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a polymer" or "at least one polymer" may include a plurality of polymers, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Materials and Methods

Materials:

Dimethylformamide was obtained from Sigma Aldrich (Israel).

Dioxane was obtained from Sigma Aldrich (Israel).

Tetrahydrofuran was obtained from Sigma Aldrich (Israel).

Poly(ε-caprolactone-co-L-lactic acid-co-glycolic acid-co-trimethylene carbonate) was obtained from/by Poly-Med Inc. (USA).

Poly(L-lactic acid) was obtained from NatureWorks (USA).

Poly(DL-lactic acid-co-ε-caprolactone) was obtained from Lactel (USA).

Poly(L-lactic acid-co-ε-caprolactone) was obtained from Purac Biomaterials (Netherlands).

Determination of Structure and Morphology:

Samples of individual sheets or 3-layer patches were coated with gold and characterized using a Quanta 200 environmental scanning electron microscope (SEM) with a tungsten filament (FEI). Fiber size and mean pore size were measured using ImageJ software.

Mechanical Properties:

Tensile tests (strain ramp) were carried out using a custom-made uniaxial tensile machine (equipped with a 25 kg load cell) in accordance with ASTM international standard D882-12 for testing tensile properties of thin plastic sheeting. Patches were cut in a dog bone configuration and thickness was measured at three points along the neck of the dog bone. The samples were immersed in PBS (phosphate buffer saline) at a temperature of 37° C. for 15 minutes before the test, and then mounted on the clamps of the machine. Each sample was stretched until breakage. The sample's Young's modulus (elastic modulus), ultimate tensile strength (UTS) and elongation at failure were determined.

Shear loss (G') and shear storage (G") modulus of the middle layer were evaluated via shear rheometer. The measurements were conducted using a strain-controlled rotational rheometer (AR-G2, TA Instruments), with a stainless steel parallel plate geometry (20 mm), which includes a Peltier temperature control. All tests were conducted at a temperature of 10° C. A strain sweep and frequency sweep tests were conducted to determine the linear viscoelastic regime of the layer. Time and temperature sweep tests were then performed at a strain range of 0.1-0.7% and a frequency of 0.05-1 Hz.

Suture Retention Test:

Suture retention tests were based on the method described in the ANSI/AAMI/ISO 7198:1998/2001/(R) 2004 standard. Samples were cut and conditioned as described hereinabove for the uniaxial tensile test. One end of the dog bone shaped sample was removed by scalpel and the sample was sutured (Premilene® 4/0 suture) at a minimum distance of 2 mm from its free end. The sample was then placed on the tensile machine, by connecting the patch to the first grip and the suture to the other grip. A tensile test was then conducted as described hereinabove, in order to measure the force at failure of the samples.

Statistical Methods:

All final values describe the average of a minimum of 3 test items. Results are expressed as the mean values±standard error.

Example 1

Electrospun Elastic Sheets

Particles of a polymer or polymer blend were dissolved in a 25:25:50 (w/w) mixture of dimethylformamide:dioxane:tetrahydrofuran to form a homogeneous solution with no aggregations. Electrospinning of the solution was conducted as depicted in FIG. 1, at a temperature of 25±5° C. and a relative humidity of 35±10%, using a syringe pump, a 22-gauge needle (inner diameter ~0.413 mm) or 23-gauge needle (inner diameter ~0.337 mm), a solution flow rate of 2.5 or 3 ml/hour, a DC voltage supply of 8 kV (±1 or 2 kV), and a tip-to-collector distance of 10±3 cm. Unwoven patches were collected on an aluminum vertical wheel (diameter 1.7 cm, width of 4.5 cm) rotating at 400 rotations per minute. The obtained sheets were dried from residual solvents by exposure to a vacuum at room temperature for 12 hours.

The following polymers were electrospun using the above general procedure (molecular weights herein refer to weight average molecular weights, except when indicated otherwise)

PLLA—poly(L-lactic acid) homopolymer (molecular weight 150±5 kDa);

PLLA/CL—poly(L-lactic acid-co-ε-caprolactone) (molar ratio 70:30 lactic acid:caprolactone, molecular weight 210±10 kDa);

PCL/LLA/GA/TMC—poly(ε-caprolactone-co-L-lactic acid-co-glycolic acid-co-trimethylene carbonate) linear block copolymer (molar ratio 35:34:17:14 caprolactone:lactic acid:glycolic acid:trimethylene carbonate, molecular weight 165±5 kDa, number average molecular weight 90±5 kDa);

Using the above general procedure and polymers, the following elastic sheets were prepared.

Example 1a

Electrospinning of a PLLA/CL solution (with a polymer concentration of 15 weight percents) was performed using a solution flow rate of 2.5 ml/hour and 23-gauge needle. The obtained sheets were 230±30 μm thick.

Figures 3A, 3B:
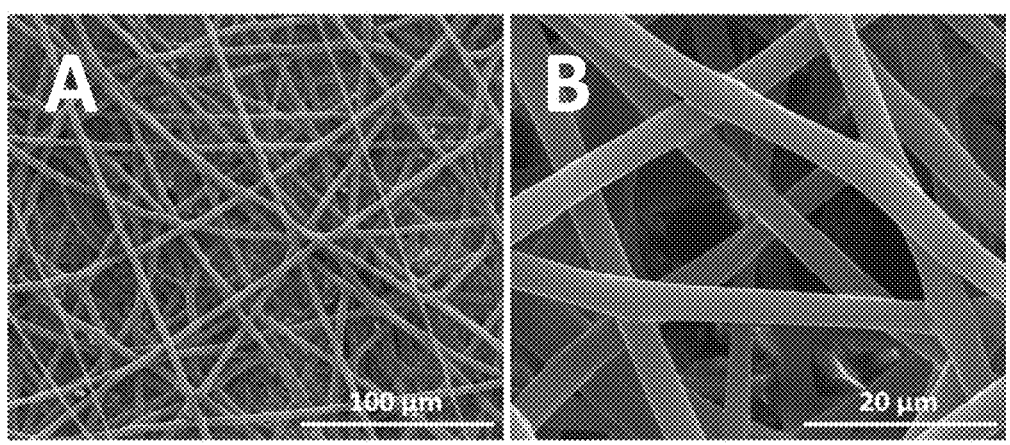
FIGS. 3A-3D present scanning electron microscopy (SEM) images of the fibers of an exemplary elastic layer according to some embodiments of the invention.

As shown in FIGS. 3A and 3B, the fibers of the sheet were smooth and had a circular cross section with a mean diameter of about 3 µm, and the pore size ranged from about 5-40 µm.

Example 1b

Electrospinning of a PLLA/CL solution (with a polymer concentration of 15 weight percents) was performed using a solution flow rate of 3 ml/hour and 22-gauge needle. The obtained sheets were 230±30 µm thick.

Figure 3C:
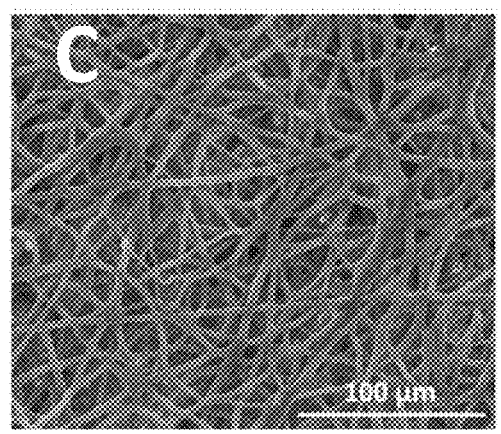
Figure 3D:
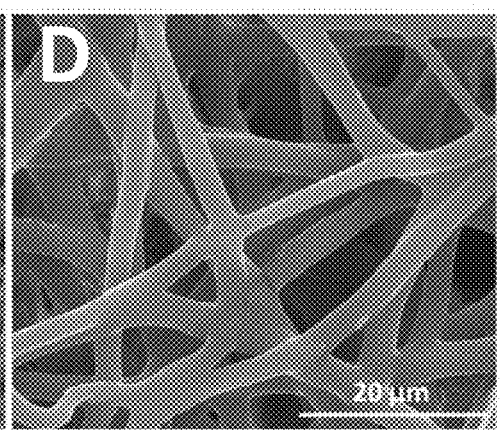

As shown in FIGS. 3C and 3D, the fibers of the sheet were morphologically more variable, and the pore size (about 2-30 µm) was somewhat smaller, as compared to Example 1a (FIGS. 3A and 3B).

Example 1c

Electrospinning of a PCL/LLA/GA/TMC solution (with a polymer concentration of 10 weight percents) was performed with a solution flow rate of 2.5 ml/hour and 23-gauge needle. The obtained sheets were 50±20 µm thick.

Example 1d

A solution of a blend of PLLA/CL and PLLA was prepared with a PLLA/CL concentration of 14 weight percents and a PLLA concentration of 1.5 weight percent, and electrospinning of the solution was performed using a solution flow rate of 2.5 ml/hour and 23-gauge needle. The obtained sheets were 160±20 µm thick.

Example 1e

A solution of a blend of PCL/LLA/GA/TMC and PLLA was prepared with a PCL/LLA/GA/TMC concentration of 10 weight percents and a PLLA concentration of 2 weight percents, and electrospinning of the solution was performed using a solution flow rate of 2.5 ml/hour and 23-gauge needle. The obtained sheets were 120±20 µm thick.

Example 2

Viscoelastic Sheets Prepared by Film Casting or Electrospinning

Example 2a

A viscoelastic sheet was prepared by a film casting technique. Particles of PDLA/CL (poly(DL-lactic acid-co-ε-caprolactone), molar ratio 25:75 lactic acid:caprolactone, molecular weight 90.1 kDa, number average molecular weight 39.4 kDa) were dissolved in tetrahydrofuran to form a homogeneous solution with no aggregations. The solution was then casted into a 5×5 cm polytetrafluoroethylene mold and vacuum dried at room temperature for 12 hours to remove residual solvents. The thickness of the obtained film was approximately 35 µm, as determined via scanning electron microscopy (SEM).

Example 2b

In an alternative procedure, viscoelastic sheets were prepared by electrospinning. Particles of PDLA/CL (poly(DL-lactic acid-co-ε-caprolactone) as described hereinabove) were dissolved at a concentration of 30 weight percents in a 25:25:50 (w/w) mixture of dimethylformamide:dioxane:tetrahydrofuran to form a homogeneous solution with no aggregations. Electrospinning of the solution was conducted at a temperature of 25±5° C. and a relative humidity of 35±10%, using a syringe pump, a 21-gauge needle (inner diameter ~0.51 mm), a solution flow rate of 2.5 ml/hour, a DC voltage supply of 8±1 kV, and a tip-to-collector distance of 10±3 cm. Unwoven patches were collected on an aluminum vertical wheel (diameter 1.7 cm, width of 4.5 cm) rotating at 400 rotations per minute. The obtained sheets were dried from residual solvents by exposure to a vacuum at room temperature for 12 hours. During this time, the fibers merged to form a film which appeared homogeneous under a light microscope.

Relatively thin sheets, characterized by thicknesses in a range of about 15-30 µm, were obtained by electrospinning 1 ml of the solution. Moderately thicker sheets, characterized by thicknesses in a range of about 40-60 µm, were obtained by electrospinning 2 ml of the solution. The thicknesses of the sheets were determined via scanning electron microscopy (SEM).

Example 2c

A viscoelastic sheet was prepared by electrospinning as described in Example 2b, except that the solution was prepared by dissolving particles of PDLA/CL (poly(DL-lactic acid-co-ε-caprolactone) as described hereinabove) and PLLA/CL (poly(L-lactic acid-co-ε-caprolactone) as described hereinabove) at a concentration of 30 weight percents PDLA/CL and 0.5 weight percent PLLA/CL. The thickness of the obtained film was approximately 30 µm, as determined via SEM.

Example 3

Integral 3-Layer Patch Prepared by Continuous Electrospinning

An integral 3-layer patch, comprising a viscoelastic layer sandwiched between two elastic layers (as depicted in FIG. 2), was prepared by continuous electrospinning. An elastic first layer comprising PLLA/CL fibers was produced as described in Example 1a. A viscoelastic second layer (middle layer) comprising PDLA/CL was then prepared as described in Example 2b by direct electrospinning, and collected on the first layer. An elastic third layer comprising PLLA/CL fibers was produced as described in Example 1a, and collected above the first and second layers. The obtained patch was vacuum dried at room temperature for 12 hours.

Figure 4A:
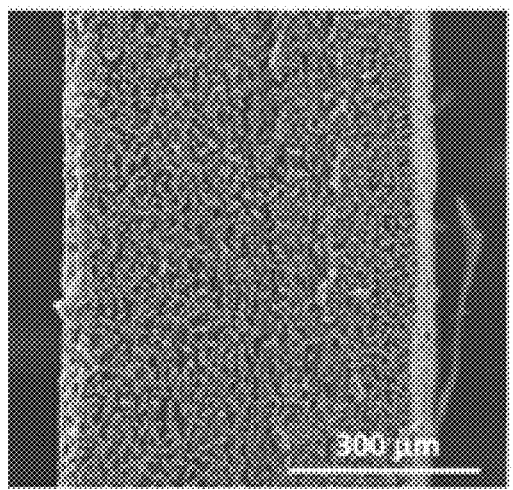
FIGS. 4A and 4B present SEM images of a cross-section of an exemplary 3-layer patch according to some embodiments of the invention (borders of the viscoelastic layer indicated in FIG. 4B by vertical white lines)
Figure 4B:
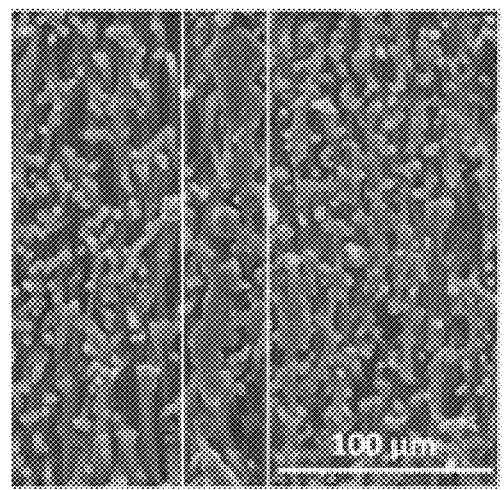

As shown in FIGS. 4A and 4B, the thickness of the obtained patch was approximately 550 µm, with the thickness of the middle layer being 25±5 µm, and the thickness of each of the elastic external layers (the first and third layers) being 230±30 µm, as determined via scanning electron microscopy (SEM).

As further shown therein, the viscoelastic middle layer retained a fibrous structure, although some merging of fibers due to diffusion of the polymer is observable.

In alternative procedures, the elastic first layer and/or third layer is prepared as described in any one of Examples 1b, 1c, 1d and 1e, rather than Example 1a.

Example 4

Integral 3-Layer Patch Prepared by Layer-by-Layer Technique

An integral 3-layer patch, comprising a viscoelastic layer sandwiched between two elastic layers (as depicted in FIG.

2), was prepared by placing a viscoelastic sheet prepared as described in Example 2 between two elastic sheets prepared as described in Example 1. The 3 sheets were heated at temperature of 40° C. for 5 minutes, and then pressed together using a pressure of 8 grams/cm². The heat increased the mobility of the polymer in the viscoelastic layer, facilitating its diffusion into the pores of the elastic layers.

Using the above general procedure, the following 3-layer patches were prepared.

Example 4a

A viscoelastic sheet comprising PDLA/CL was prepared by electrospinning 1 ml of solution as described in Example 2b, and sandwiched between two electrospun elastic sheets comprising electrospun PLLA/CL, which were prepared as described in Example 1a. The obtained patch was approximately 500 μm thick, as determined by scanning electron microscopy (SEM).

Figures 5A, 5B, 5C:
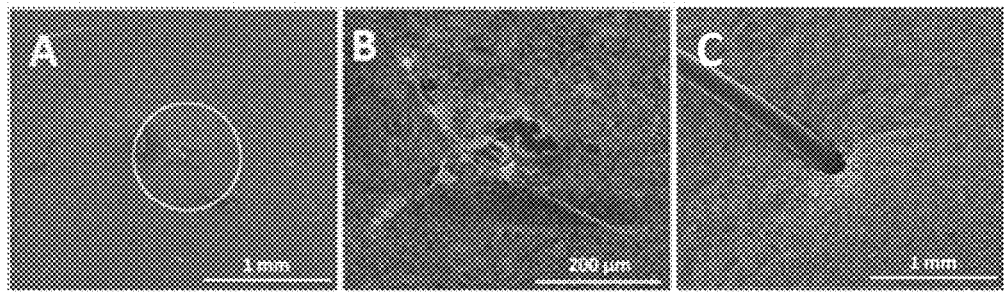
FIGS. 5A-5F present SEM images of a puncture formed by a suture needle (FIGS. 5A and 5B, circle in FIG. 5A indicates location of puncture), a monofilament suture (FIG. 5C) and braided suture (FIG. 5D) in an exemplary 3-layer patch according to some embodiments of the invention, and a cross-section of the 3-layer patch (FIGS. 5E and 5F) (white rectangle in FIG. 5F shows higher magnification, borders of the viscoelastic layer indicated by vertical white lines)

As shown in FIGS. 5A and 5B, a suture hole in the patch created by a 4-0 Monocryl® suture (Ethicon) was substantially closed by the elasticity of the elastic layer.

Figures 5D, 5E, 5F:
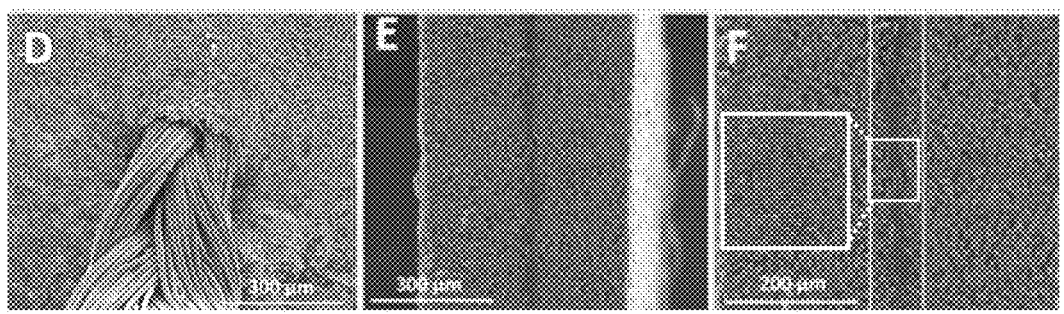

Similarly, as shown in FIGS. 5C and 5D, the elastic layer closed tightly around a polypropylene monofilament 4/0 (Premilene®) suture (FIG. 5C) and poly(glycolic acid) braided 4/0 suture (FIG. 5D) left in place.

As shown in FIGS. 5E and 5F, the structure of the elastic layer was characterized by distinct fibers, whereas the viscoelastic layer formed a continuous film (with a thickness of about 25 μm) due to merging of the fibers therein.

As further shown in FIG. 5F, the polymer of the viscoelastic layer partially diffused into the elastic layer (probably during the application of pressure and heat).

An additional patch was prepared using a viscoelastic sheet prepared as described in Example 2b, with twice as much polymer solution (2 ml instead of 1 ml).

Example 4b

A viscoelastic sheet comprising electrospun PDLA/CL and PLLA/CL was prepared by electrospinning as described in Example 2c, and sandwiched between two electrospun elastic sheets comprising PLLA/CL, which were prepared as described in Example 1a. The patch was then vacuum-dried for 12 hours at room temperature. The obtained patch was approximately 525 μm thick, as determined by SEM.

Example 4c

A viscoelastic sheet comprising PDLA/CL was prepared by film casting as described in Example 2a, and sandwiched between two electrospun elastic sheets comprising PLLA/CL, which were prepared as described in Example 1a. The obtained patch was approximately 490 μm thick, as determined by SEM.

In alternative procedures, using the above general procedure, a viscoelastic sheet prepared according to any one of Examples 2a, 3b and 2c is sandwiched between two elastic sheets prepared as described in any one of Examples 1b, 1c, 1d and 1e, rather than Example 1a.

Example 5

Mechanical Properties of Layers and 3-Layer Patches

The Young's modulus at strains of 50-125% (10-25 mm extension), ultimate tensile strength and elongation at failure were determined for single-layer elastic sheets prepared as described in each of Examples 1a-1e, and for 3-layered patches prepared as described in each of Examples 3-4c, using procedures described in the Materials and Methods section hereinabove. The results are presented in Table 1 below.

TABLE 1

Mechanical properties of single-layer elastic sheets and 3-layer patches
(mean ± standard deviation of 3 measurements per sample)

| | Example No. | | | | | | | | |
|---|---|---|---|---|---|---|---|---|---|
| | Elastic sheets (Example 1) | | | | | 3-layer patches (Examples 3 & 4) | | | |
| | 1a | 1b | 1c | 1d | 1e | 3 | 4a | 4b | 4c |
| Young's modulus [MPa] | 0.25 ± 0.04 | 0.32 ± 0.05 | 0.74 ± 0.14 | 0.715 ± 0.09 | 0.762 ± 0.09 | 0.35 ± 0.1 | 0.22 ± 0.05 | 0.194 ± 0.05 | 0.11 ± 0.02 |
| UTS [MPa] | 5.3 ± 0.18 | 6.3 ± 0.28 | 6.8 ± 0.84 | 5.3 ± 0.73 | 5.0 ± 0.34 | 5.3 ± 0.46 | 4.6 ± 1.3 | 3.6 ± 1.02 | 4.5 ± 0.91 |
| Elongation [%] | 386 ± 9 | 342 ± 22 | 493 ± 32 | 261 ± 31 | 407 ± 34 | 439 ± 24 | 507 ± 66 | 541 ± 106 | 449 ± 27 |

Figures 6A, 6B, 6C:
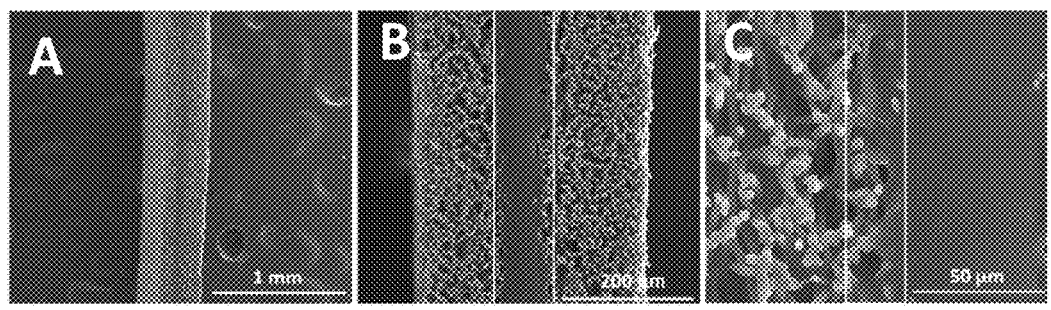
FIGS. 6A-6C present SEM images of a cross-section of an exemplary 3-layer patch according to some embodiments of the invention (borders of the viscoelastic layer indicated in FIGS. 6B and 6C by vertical white lines)

As shown in FIGS. 6A-6C, the viscoelastic layer prepared with 2 ml polymer solution was characterized by a thickness of about 50 μm, as compared with 25 μm the viscoelastic layer prepared with 1 ml polymer solution (as shown in FIGS. 5E and 5F).

In order to determine the ability of the patches to retain sutures, a suture retention test was performed as described in the Materials and Methods section hereinabove.

The mean force applied to a suture in a 3-layer patch until failure of the patch was 237.8±8.7 grams force. This result indicates that a sutured 3-layer patch exhibits satisfactory mechanical strength and ability to retain sutures.

As shown in Table 1, all of the samples exhibited low Young's modulus values, indicating an ability to readily undergo deformation immediately upon loading, as well as an ability to undergo considerable elongation (about 250-550%) before breaking. As further shown therein, the mechanical properties of the 3-layer patches were similar to those of the elastic sheets incorporated within the patches (the elastic sheet of Example 1a).

These results indicate that the elastic layers and patches containing them exhibit mechanical properties similar to those of some biological fibers, such as elastin and resilin, which exhibit a Young's modulus on the order of a few MPa and elongation of above 100%.

In order to evaluate the properties of the viscoelastic layer, the shear storage modulus (G') and shear loss modulus (G") of a viscoelastic sheet prepared as described in Example 2a were determined by oscillatory shear tests, as described in the Materials and Methods section hereinabove. The ratio of G" to G' can be expressed as the loss tangent (G"/G') or as the phase angle (arctangent of G"/G'), wherein a relatively high loss tangent (and phase angle approaching 90°) indicates viscous, liquid-like properties, whereas a relatively low loss tangent (and phase angle approaching 0°) indicates more elastic and solid-like properties.

The viscoelastic layers exhibited a phase angle in a range of from 10.2° to 25.87°, corresponding to a loss tangent in a range of from 0.180 to 0.485.

These results indicate that the viscoelastic layers exhibit gel-like behavior, wherein there is a significant degree of viscous, liquid-like behavior, but elastic, solid-like properties predominate (e.g., G'>G").

Example 6

Water-Permeability of Layers and 3-Layer Patches

In order to evaluate the water-permeability of 3-layered patches prepared as described herein, as well as the effect of each layer on water-permeability, the water-permeability of the following materials was tested:
1) an electrospun elastic sheet prepared as described in Example 1a;
2) a double elastic layer, prepared by pressing together two electrospun elastic sheets (prepared as described in Example 1a) according to the procedures described in Example 4, but without a viscoelastic middle layer;
3) a 3-layer patch prepared by continuous electrospinning, as described in Example 3;
4) a 3-layer patch prepared by pressing together from 3 sheets, as described in Example 4a;
5) a 3-layer patch as described in Example 4a, sutured once using a poly(glycolic acid) 4/0 suture and a 19 mm ⅜ needle, the suture remaining in the patch;
6) a 3.5 mm thick Duragen™ suturable collagen dural substitute (Integra), for comparison.

Testing was performed in accordance with ISO 811, with several modifications. Test items were inserted into a custom-made testing apparatus made of Plexiglas®. The apparatus was comprised of an inlet tube (inner diameter 1.7 cm) filled with saline at 37° C., to the desired height. The test item was placed at the bottom of the inlet tube, and was held in place by two rubber rings with an inner diameter equal to that of the tube. Saline was added to the inlet tube such that the surface area of the test item exposed to the saline was 9 cm². During testing, the apparatus was maintained at a steady temperature of 37° C. The amount of saline that passed the item into the outlet tube was measured during the course of 30 minutes. To verify a constant pressure the level of fluid in the tube was kept constant. The degree of water-permeability was determined by comparing the amount of saline that passed the items into the outlet tube. Two levels of pressures were tested: 1) 15 mmHg, which corresponds to the normal intracranial CSF pressure; and 2) 40 mmHg, which corresponds to higher than normal intracranial pressure.

As shown in FIG. 7, the single elastic layers, and to a lesser extent, the double elastic layers, exhibited some leakage which was correlated with pressure, whereas the 3-layer patches prepared as described in Example 4a exhibited no leakage at either tested pressure.

These results indicate that the viscoelastic middle layer provided a high degree of water-impermeability, whereas the elastic layers are porous and somewhat water-permeable.

As further shown in FIG. 7, the 3-layer patches prepared as described in Example 3 were considerably more water-impermeable than the single or double elastic layer, but exhibited slight leakage. This result is in accordance with the above-described finding that the viscoelastic layer in these 3-layer patches retained a partially porous fibrous structure, in contrast to the more continuous structure of the viscoelastic layer in 3-layer patches prepared as described in Example 4a.

As further shown therein, the presence of a suture in a 3-layer patch did not result in leakage at relatively low pressure (15 mmHg), and resulted in only a very small degree of leakage at higher pressure (40 mmHg).

These results suggest that the patch effectively closes tightly around the suture, thereby minimizing leakage at the location of the suture.

As further shown in FIG. 7, the collagen dural substitute exhibited the highest rate of leakage by far, despite being the thickest material tested. The entire column of saline leaked through the collagen dural substitute within less than 5 minutes.

This result indicates that the elastic layers in a patch are also relatively water-impermeable, in comparison with a collagen dural substitute.

Example 7

Layered Patches with Tissue-Interactive Additives

A patch comprising one or more additives is prepared using a core matrix comprising elastic layers and a viscoelastic layer, corresponding to a 3-layer patch as described in any one of Examples 3 and 4, and one or more additives on a surface of the core matrix, such that additive(s) can directly contact tissue onto which the patch is applied. The additive(s) is selected to be adhesive, thereby allowing the patch to adhere to tissue without sutures, and/or selected to facilitate cell attachment and/or proliferation on the patch surface. The core matrix provides the patch with water-impermeability and mechanical strength and resilience.

An additive is optionally a substance applied onto the core matrix and optionally a product of surface modification of the core matrix.

An additive selected to be adhesive is optionally a surface modification technique such as plasma surface treatment (optionally with oxygen plasma, ammonia plasma, argon plasma or air plasma), exposure to flames, mechanical treatment, corona discharge, wet-chemical treatment and/or surface grafting (e.g., of monomers or polymers, optionally poly(N-isopropylacrylamide), poly(acrylic acid) and/or poly (amino acids)).

The surface modification (e.g., plasma surface treatment, surface grafting) optionally increases the hydrophilicity of a surface of the patch by altering the electrostatic charge of the surface.

An additive selected to be adhesive is optionally an adhesive substance (e.g., synthetic or biological in origin) in dry form, which is applied by coating at least a portion of the surface of the core matrix with the adhesive additive. The adhesiveness of the substance is enhanced upon hydration, for example, upon contact with moist tissue. The adhesive additive is optionally a dry combination of thrombin and fibrinogen (which interact upon hydration to form fibrin), an albumin coating (optionally formed by electrospinning), and/or a polymer (optionally a polysaccharide, poly(vinyl acetate) and/or poly(vinyl pyrrolidone)) which includes a functional group (optionally an imido ester, p-nitrophenyl carbonate, N-hydroxysuccinimide (NHS) ester, epoxide, isocyanate, acrylate, vinyl sulfone, orthopyridyl-disulfide, maleimide, aldehyde and/or iodoacetamide group) that can react with a surface protein to form a covalent bond.

The amount of adhesive is optionally controlled such that the adhesion strength of the patch (as evaluated by the lap shear strength of a patch adhered to a biological fascia measured by a uniaxial tensile test) is in a range of from 10 to 30 kPa.

An additive selected to facilitate cell attachment and/or proliferation is optionally a coating of growth factors and/or a layer (optionally having a thickness in a range of from 50 to 400 μm) of biocompatible nanofibers, optionally formed by electrospinning. The nanofibers are optionally composed of synthetic polymers and/or co-polymers (e.g. polyesters) and/or biological polymers (e.g., gelatin, collagen, elastin, laminin and/or fibronectin).

Example 8

Layered Patches with Anti-Adhesive Additives

A patch comprising one or more additives is prepared using a core matrix comprising elastic layers and a viscoelastic layer, corresponding to a 3-layer patch as described in any one of Examples 3 and 4, and one or more additives on a surface of the core matrix, such that additive(s) can directly contact tissue onto which the patch is applied. The additive(s) is selected to reduce undesirable tissue adhesion to the patch surface. The core matrix provides the patch with water-impermeability and mechanical strength and resilience.

The additive(s) is in a form of a layer (optionally having a thickness in a range of from 10 to 400 μm) of nanofibers (e.g., which exhibit anti-fouling properties), optionally formed by electrospinning. The nanofibers are optionally composed of poly(ethylene glycol) and/or co-polymers comprising poly(ethylene glycol).

Example 9

Use of Layered Patch as a Dural Substitute

A layered patch as described in any one of Examples 3, 4, 7 and 8 is used to prevent cerebrospinal fluid (CSF) leakage through a damaged dura mater (e.g., damaged by trauma or surgery requiring breach of the dura mater).

The patch is optionally positioned between the dura mater and neural tissue (e.g., brain) such that it overlays edges of a breached dura mater, covering the breach in the dura mater.

Optionally, the patch comprises one or more additive selected to be adhesive and/or to facilitate cell attachment and/or proliferation on the patch surface, as described in Example 7, on a surface which is positioned adjacent to the dura mater and/or skull (e.g., on the side of the patch which faces away from the brain), thereby preferentially adhering to and/or facilitating cell attachment and/or proliferation in the dura mater and/or tissue adjacent to the skull, rather than in neural tissue (e.g., the brain).

Additionally or alternatively, the patch comprises one or more anti-adhesive additive as described in Example 8, on a surface which is positioned adjacent to the neural tissue (e.g., on the side of the patch which faces towards the brain), thereby reducing and optionally preventing adhesion of the patch to neural tissue.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A composition-of-matter comprising a multi-layer matrix, said matrix comprising at least one layer of an elastic polymeric material and at least one layer of a viscoelastic polymeric material, wherein at least one layer of said elastic polymeric material is in a form of a porous layer of polymeric fibers, and wherein said viscoelastic polymeric material comprises a polymer characterized by a glass transition temperature and/or melting point at a temperature below 40° C., said elastic polymeric material comprises a polymer characterized by a glass transition temperature and/or melting point at a temperature above 40° C., and wherein said layer of said viscoelastic polymeric material is characterized by a loss tangent (G"/G') at a temperature of 10° C. and frequency of 0.1 Hz which is in a range of from 0.01 to 4.

2. The composition-of-matter of claim 1, comprising at least two layers of said elastic polymeric material, each of said layers is independently in a form of a porous layer of polymeric fibers, wherein said layer of a viscoelastic polymeric material is interposed between two of said layers of an elastic polymeric material.

3. The composition-of-matter of claim 1, wherein each layer of said elastic polymeric material is a porous layer characterized by a porosity of at least 50%.

4. The composition-of-matter of claim 1, wherein said polymeric fibers are characterized by a mean diameter in a range of from 0.001 to 30 μm.

5. The composition-of-matter of claim 1, wherein said layer of a viscoelastic polymeric material is characterized by at least one of:
   a) a storage shear modulus (G') in a range of from 0.01 to 10 MPa, at a temperature of 10° C. and frequency of 0.1 Hz; and
   b) a loss shear modulus (G") in a range of from 0.0001 to 2 MPa, at a temperature of 10° C. and frequency of 0.1 Hz.

6. The composition-of-matter of claim 1, wherein polymeric fibers comprise electrospun elastic polymeric material.

7. The composition-of-matter of claim 1, wherein said layer of a viscoelastic polymeric material is characterized by a porosity in a range of from 0 to 50%.

8. The composition-of-matter of claim 1, wherein said elastic polymeric material is biocompatible.

9. The composition-of-matter of claim 1, wherein said matrix is characterized by a thickness of less than 3 mm.

10. The composition-of-matter of claim 1, wherein each of said layers of an elastic polymeric material is characterized by an elastic modulus in a range of from 1 kPa to 10 MPa, as determined in accordance with ASTM international standard D882-12.

11. The composition-of-matter of claim 1, wherein each of said layers of an elastic polymeric material is characterized by an elongation at failure of at least 100%.

12. The composition-of-matter of claim 1, wherein each of said layers of an elastic polymeric material is characterized by an ultimate tensile strength of at least 0.05 MPa.

13. The composition-of-matter of claim 1, wherein said matrix is characterized by an elastic modulus which is within a range of 80% to 120% of an elastic modulus of at least one of said elastic layers.

14. The composition-of-matter of claim 1, wherein at least one of said layers of an elastic polymeric material comprises an electrospun polymeric material.

15. The composition-of-matter of claim 1, wherein said viscoelastic polymeric material comprises poly(lactic acid-co-ε-caprolactone).

16. The composition-of-matter of claim 1, wherein said matrix is characterized by a water-permeability of less than 1 ml per hour per $cm^2$ upon exposure to an aqueous liquid at a pressure of 40 mmHg.

17. The composition-of-matter of claim 1, further comprising at least one additional ingredient, said additional ingredient being in a form of an additional layer on at least a portion of at least one surface of said matrix and/or dispersed within and/or on at least one surface of said matrix, said at least one additional ingredient imparting an additional functionality.

18. The composition-of-matter of claim 1, being a suturable and/or stapleable matrix capable of self-recovery.

19. An article-of-manufacture comprising the composition-of-matter or matrix of claim 1, the article-of-manufacture being a medical device.

20. A method of repairing and/or substituting a biological tissue in a subject in need thereof, the method comprising contacting the biological tissue with the article-of-manufacture of claim 19, thereby repairing and/or substituting the biological tissue.

21. The method of claim 20, wherein said repairing and/or substituting a biological tissue comprises suturing and/or stapling the article-of-manufacture to the tissue.

22. A process for preparing the composition-of-matter of claim 1, the process comprising forming said layers of an elastic polymeric material and said at least one layer of a polymeric viscoelastic layer by continuous electrospinning.

23. A process for preparing the composition-of-matter of claim 1, the process comprising forming said layers of an elastic polymeric material by electrospinning, placing said at least one layer of a viscoelastic polymeric material parallel to said layers of an elastic polymeric material, and pressing said layers of an elastic polymeric material and said at least one layer of a viscoelastic polymeric material together, thereby forming said composition-of-matter.

24. A composition-of-matter comprising a multi-layer, suturable and/or stapleable matrix, said matrix comprising (i) at least one layer of an elastic polymeric material characterized by a recovery of at least 75%, and (ii) at least one layer of a viscoelastic polymeric material characterized by a loss tangent (G"/G') at a temperature of 10° C. and frequency of 0.1 Hz which is in a range of from 0.02 to 1.

25. The composition-of-matter of claim 24, wherein said at least one layer of an elastic polymeric material is a porous layer characterized by a porosity of at least 50%.

26. The composition-of-matter of claim 24, wherein said at least one layer of an elastic polymeric material comprises polymeric fibers.

27. The composition-of-matter of claim 24, wherein at least one layer of said viscoelastic polymeric material is interposed between two layers of said elastic polymeric material.

28. The composition-of-matter of claim 24, wherein said layer of a viscoelastic polymeric material is characterized by at least one of:
 a) a storage shear modulus (G') in a range of from 0.01 to 10 MPa, at a temperature of 10° C. and frequency of 0.1 Hz;
 b) a loss shear modulus (G") in a range of from 0.0001 to 2 MPa, at a temperature of 10° C. and frequency of 0.1 Hz; and
 c) a glass transition temperature and/or melting point of said viscoelastic polymeric material which is at a temperature below 40° C.

29. The composition-of-matter of claim 24, wherein each of said layers of an elastic polymeric material is characterized by an elastic modulus in a range of from 1 kPa to 10 MPa, as determined in accordance with ASTM international standard D882-12.

30. The composition-of-matter of claim 24, wherein said matrix is characterized by a water-permeability of less than 1 ml per hour per $cm^2$ upon exposure to an aqueous liquid at a pressure of 40 mmHg.

31. An article-of-manufacture comprising the composition-of-matter or matrix of claim 24, the article-of-manufacture being a medical device.

32. A method of repairing and/or substituting a biological tissue in a subject in need thereof, the method comprising contacting the biological tissue with the article-of-manufacture of claim 31, thereby repairing and/or substituting the biological tissue.

33. A composition-of-matter comprising a multi-layer, suturable and/or stapleable matrix, said matrix comprising at least one layer of an elastic polymeric material characterized by a recovery of at least 75%, and at least one layer of a viscoelastic polymeric material,
wherein said layer of a viscoelastic polymeric material is characterized by at least one of:
 a) a storage shear modulus (G') in a range of from 0.01 to 10 MPa, at a temperature of 10° C. and frequency of 0.1 Hz;
 b) a loss shear modulus (G") in a range of from 0.0001 to 2 MPa, at a temperature of 10° C. and frequency of 0.1 Hz;
 c) a glass transition temperature and/or melting point of said viscoelastic polymeric material which is at a temperature below 40° C.; and
 d) a loss tangent (G"/G') at a temperature of 10° C. and frequency of 0.1 Hz which is in a range of from 0.02 to 1,
and wherein said layer of an elastic polymeric material is characterized by at least one of:
 a) an elastic modulus in a range of from 1 kPa to 10 MPa, as determined in accordance with ASTM international standard D882-12;
 b) an elongation at failure in a range of at least 100%; and
 c) a glass transition temperature and/or melting point of said elastic polymeric material which is at a temperature above 40° C.

* * * * *